United States Patent
Devane et al.

(10) Patent No.: US 8,119,163 B2
(45) Date of Patent: Feb. 21, 2012

(54) NANOPARTICULATE AND CONTROLLED RELEASE COMPOSITIONS COMPRISING CEFDITOREN

(75) Inventors: John G Devane, Athlone (IE); Paul Stark, Glasson (IE); Niall M. N. Fanning, Raheny (IE); Gurvinder Singh Rekhi, Suwanee, GA (US); Scott A. Jenkins, Downingtown, PA (US); Gary Liversidge, West Chester, PA (US)

(73) Assignee: Alkermes Pharma Ireland Limited, Dublin (IE)

( * ) Notice: Subject to any disclaimer, the term of this patent is extended or adjusted under 35 U.S.C. 154(b) by 850 days.

(21) Appl. No.: 11/671,276

(22) Filed: Feb. 5, 2007

(65) Prior Publication Data
US 2008/0279929 A1    Nov. 13, 2008

Related U.S. Application Data

(63) Continuation of application No. 11/449,005, filed on Jun. 7, 2006, now abandoned, which is a continuation-in-part of application No. 11/372,857, filed on Mar. 10, 2006, which is a continuation-in-part of application No. 10/827,689, filed on Apr. 19, 2004, which is a continuation of application No. 10/354,483, filed on Jan. 30, 2003, now Pat. No. 6,793,936, which is a continuation of application No. 10/331,754, filed on Dec. 30, 2002, now Pat. No. 6,902,742, which is a continuation of application No. 09/850,425, filed on May 7, 2001, now Pat. No. 6,730,325, which is a continuation of application No. 09/566,636, filed on May 8, 2000, now Pat. No. 6,228,398, which is a continuation of application No. PCT/US99/25632, filed on Nov. 1, 1999.

(60) Provisional application No. 60/106,726, filed on Nov. 2, 1998.

(51) Int. Cl.
*A61K 9/14* (2006.01)
*A61K 9/16* (2006.01)
*A61K 9/50* (2006.01)
*A61K 9/54* (2006.01)

(52) U.S. Cl. ........ 424/489; 424/456; 424/458; 424/469; 424/490

(58) Field of Classification Search ................ None
See application file for complete search history.

(56) References Cited

U.S. PATENT DOCUMENTS

| | | | |
|---|---|---|---|
| 3,424,839 A | 1/1969 | Montandraud | |
| 4,330,626 A | 5/1982 | Blair et al. | |
| 4,539,199 A | 9/1985 | Orban et al. | |
| 4,708,874 A | 11/1987 | De Haan et al. | |
| 4,728,512 A | 3/1988 | Mehta et al. | |
| 4,783,484 A | 11/1988 | Violante et al. | |
| 4,794,001 A | 12/1988 | Mehta et al. | |
| 4,826,689 A | 5/1989 | Violante et al. | |
| 4,844,896 A | 7/1989 | Bohm et al. | |
| 4,851,228 A | 7/1989 | Zentner et al. | |
| 4,882,166 A | 11/1989 | Graham et al. | |
| 4,888,178 A | 12/1989 | Rotini et al. | |
| 4,892,742 A | 1/1990 | Shah | |
| 4,904,476 A | 2/1990 | Mehta et al. | |
| 4,940,588 A | 7/1990 | Sparks et al. | |
| 4,948,586 A | 8/1990 | Bohm et al. | |
| 4,952,402 A | 8/1990 | Sparks et al. | |
| 4,971,790 A | 11/1990 | Magruder et al. | |
| 4,971,805 A | 11/1990 | Kitanishi et al. | |
| 4,986,987 A | 1/1991 | Ayer et al. | |
| 4,997,454 A | 3/1991 | Violante et al. | |
| 5,102,668 A | 4/1992 | Eichel et al. | |
| 5,133,974 A | 7/1992 | Paradissis et al. | |
| 5,145,684 A * | 9/1992 | Liversidge et al. | ........... 424/489 |
| 5,158,777 A | 10/1992 | Abramowitz et al. | |
| 5,162,117 A | 11/1992 | Stupak et al. | |
| 5,196,203 A | 3/1993 | Boehm | |
| 5,202,128 A | 4/1993 | Morella et al. | |
| 5,226,902 A | 7/1993 | Bae et al. | |
| 5,229,131 A | 7/1993 | Amidon et al. | |
| 5,232,705 A | 8/1993 | Wong et al. | |
| 5,260,068 A | 11/1993 | Chen | |
| 5,260,069 A | 11/1993 | Chen | |
| 5,262,173 A | 11/1993 | Sheth et al. | |
| 5,298,262 A | 3/1994 | Na et al. | |

(Continued)

FOREIGN PATENT DOCUMENTS

DE    3229876 A1    3/1983

(Continued)

OTHER PUBLICATIONS

Lindahl et al., "Characterization of Fluids from the Stomach and Proximal Jejunum in Men and Women," Pharm, Res., 14(4): 497-502 (1997).

(Continued)

*Primary Examiner* — Robert A Wax
*Assistant Examiner* — Olga V Tcherkasskaya
(74) *Attorney, Agent, or Firm* — Fox Rothschild LLP

(57) ABSTRACT

The present invention provides a composition comprising a cefditoren, or a salt, derivative, prodrug, or other form thereof, for example, cefditoren pivoxil, useful in the treatment and prevention of infections and related conditions. The invention provides a composition which comprises nanoparticulate particles comprising the cefditoren, or a salt, derivative, prodrug, or other form thereof and at least one surface stabilizer. The nanoparticulate particles have an effective average particle size of less than about 2000 nm. The invention provides also a composition that delivers a cefditoren, or a salt, derivative, prodrug, or other form thereof, or nanoparticles comprising the same, in a pulsatile or continuous manner.

22 Claims, No Drawings

U.S. PATENT DOCUMENTS

| | | | |
|---|---|---|---|
| 5,302,401 A | 4/1994 | Liversidge et al. | |
| 5,318,767 A | 6/1994 | Liversidge et al. | |
| 5,326,552 A | 7/1994 | Na et al. | |
| 5,328,404 A | 7/1994 | Bacon | |
| 5,330,759 A | 7/1994 | Pagay et al. | |
| 5,330,766 A | 7/1994 | Morella et al. | |
| 5,336,507 A | 8/1994 | Na et al. | |
| 5,340,564 A | 8/1994 | Illig et al. | |
| 5,346,702 A | 9/1994 | Na et al. | |
| 5,349,957 A | 9/1994 | Yudelson | |
| 5,352,459 A | 10/1994 | Hollister et al. | |
| 5,354,556 A | 10/1994 | Sparks et al. | |
| 5,378,474 A | 1/1995 | Morella et al. | |
| 5,380,790 A | 1/1995 | Chen et al. | |
| 5,384,124 A | 1/1995 | Courteille et al. | |
| 5,387,421 A | 2/1995 | Amidon et al. | |
| 5,395,628 A | 3/1995 | Noda et al. | |
| 5,399,363 A | 3/1995 | Liversidge et al. | |
| 5,401,492 A | 3/1995 | Kellar et al. | |
| 5,401,512 A | 3/1995 | Rhodes et al. | |
| 5,411,745 A | 5/1995 | Oshlack et al. | |
| 5,425,950 A | 6/1995 | Dandiker et al. | |
| 5,429,824 A | 7/1995 | June | |
| 5,436,011 A | 7/1995 | Dennis et al. | |
| 5,439,689 A | 8/1995 | Hendrickson et al. | |
| 5,445,828 A | 8/1995 | Pozzi et al. | |
| 5,445,829 A | 8/1995 | Paradissis et al. | |
| 5,447,710 A | 9/1995 | Na et al. | |
| 5,451,393 A | 9/1995 | Liversidge et al. | |
| 5,460,817 A | 10/1995 | Langley et al. | |
| 5,466,440 A | 11/1995 | Ruddy et al. | |
| 5,470,583 A | 11/1995 | Na et al. | |
| 5,472,683 A | 12/1995 | Illig | |
| 5,472,708 A | 12/1995 | Chen | |
| 5,484,608 A | 1/1996 | Rudnic et al. | |
| 5,494,683 A | 2/1996 | Liversidge et al. | |
| 5,500,204 A | 3/1996 | Osifo | |
| RE35,200 E | 4/1996 | Lehmann et al. | |
| 5,508,040 A | 4/1996 | Chen | |
| 5,510,118 A | 4/1996 | Bosch et al. | |
| 5,518,187 A | 5/1996 | Bruno et al. | |
| 5,518,738 A | 5/1996 | Eickhoff et al. | |
| 5,521,218 A | 5/1996 | Osifo | |
| 5,525,328 A | 6/1996 | Bacon et al. | |
| 5,534,263 A | 7/1996 | Wong et al. | |
| 5,534,270 A | 7/1996 | De Castro | |
| 5,543,133 A | 8/1996 | Swanson et al. | |
| 5,552,160 A | 9/1996 | Liversidge et al. | |
| 5,560,931 A | 10/1996 | Eickhoff et al. | |
| 5,560,932 A | 10/1996 | Bagchi et al. | |
| 5,565,188 A | 10/1996 | Wong et al. | |
| 5,569,448 A | 10/1996 | Wong et al. | |
| 5,571,536 A | 11/1996 | Eickhoff et al. | |
| 5,573,749 A | 11/1996 | Illig | |
| 5,573,750 A | 11/1996 | Singh | |
| 5,573,783 A * | 11/1996 | Desieno et al. | 424/490 |
| 5,580,579 A | 12/1996 | Ruddy et al. | |
| 5,585,108 A | 12/1996 | Ruddy et al. | |
| 5,587,143 A | 12/1996 | Wong | |
| 5,591,456 A | 1/1997 | Franson et al. | |
| 5,593,657 A | 1/1997 | Ruddy et al. | |
| 5,593,694 A | 1/1997 | Hayashida et al. | |
| 5,622,938 A | 4/1997 | Wong | |
| 5,628,981 A | 5/1997 | Liversidge et al. | |
| 5,629,017 A | 5/1997 | Pozzi et al. | |
| 5,639,476 A | 6/1997 | Oshlack et al. | |
| 5,643,552 A | 7/1997 | Illig | |
| 5,654,006 A | 8/1997 | Fernandez et al. | |
| 5,662,883 A | 9/1997 | Bagchi et al. | |
| 5,665,331 A | 9/1997 | Bagchi et al. | |
| 5,681,584 A | 10/1997 | Savastano et al. | |
| 5,716,981 A | 2/1998 | Hunter et al. | |
| 5,718,388 A | 2/1998 | Czekai et al. | |
| 5,718,919 A | 2/1998 | Ruddy et al. | |
| 5,726,316 A | 3/1998 | Crooks et al. | |
| 5,736,161 A | 4/1998 | Garces et al. | |
| 5,741,522 A | 4/1998 | Violante et al. | |
| 5,747,001 A | 5/1998 | Wiedmann et al. | |
| 5,753,261 A | 5/1998 | Fernandez et al. | |
| 5,763,452 A | 6/1998 | Miller et al. | |
| 5,776,496 A | 7/1998 | Violante et al. | |
| 5,776,856 A | 7/1998 | Narayanan | |
| 5,807,579 A | 9/1998 | Vilkov et al. | |
| 5,820,879 A | 10/1998 | Fernandez et al. | |
| 5,820,883 A | 10/1998 | Tice et al. | |
| 5,834,023 A | 11/1998 | Chen | |
| 5,834,024 A | 11/1998 | Heinicke et al. | |
| 5,837,284 A | 11/1998 | Mehta et al. | |
| 5,840,329 A | 11/1998 | Bai | |
| 5,840,332 A | 11/1998 | Lerner et al. | |
| 5,862,999 A | 1/1999 | Czekai et al. | |
| 5,872,104 A | 2/1999 | Vermeulen et al. | |
| 5,874,090 A | 2/1999 | Baker et al. | |
| 5,885,616 A | 3/1999 | Hsiao et al. | |
| 5,908,850 A | 6/1999 | Zeitlin et al. | |
| 5,958,458 A | 9/1999 | Norling et al. | |
| 5,958,915 A * | 9/1999 | Abe et al. | 514/206 |
| 6,004,584 A | 12/1999 | Peterson et al. | |
| 6,025,502 A | 2/2000 | Winklter et al. | |
| 6,045,829 A | 4/2000 | Liversidge et al. | |
| 6,066,292 A | 5/2000 | Purwar | |
| 6,068,858 A | 5/2000 | Liversidge et al. | |
| 6,096,148 A | 8/2000 | Kingma | |
| 6,114,423 A | 9/2000 | Eck et al. | |
| 6,117,455 A | 9/2000 | Takada et al. | |
| 6,123,923 A | 9/2000 | Unger et al. | |
| 6,153,225 A | 11/2000 | Lee et al. | |
| 6,156,342 A | 12/2000 | Sriwongjanya et al. | |
| 6,165,506 A | 12/2000 | Jain et al. | |
| 6,183,780 B1 | 2/2001 | Van Balken et al. | |
| 6,217,904 B1 | 4/2001 | Midha et al. | |
| 6,221,400 B1 | 4/2001 | Liversidge et al. | |
| 6,228,398 B1 | 5/2001 | Devane et al. | |
| 6,264,922 B1 | 7/2001 | Wood et al. | |
| 6,267,989 B1 | 7/2001 | Liversidge et al. | |
| 6,270,806 B1 | 8/2001 | Liversidge et al. | |
| 6,294,591 B1 | 9/2001 | Blum et al. | |
| 6,300,403 B1 | 10/2001 | Mayer et al. | |
| 6,316,029 B1 | 11/2001 | Jain et al. | |
| 6,322,819 B1 | 11/2001 | Burnside et al. | |
| 6,327,254 B1 | 12/2001 | Chuah | |
| 6,340,476 B1 | 1/2002 | Midha et al. | |
| 6,344,215 B1 | 2/2002 | Bettman et al. | |
| 6,346,216 B1 | 2/2002 | Kent | |
| 6,372,254 B1 | 4/2002 | Ting et al. | |
| 6,375,986 B1 | 4/2002 | Ryde et al. | |
| 6,419,952 B2 | 7/2002 | Wong et al. | |
| 6,419,960 B1 | 7/2002 | Krishnamurthy et al. | |
| 6,428,814 B1 | 8/2002 | Bosch | |
| 6,431,478 B1 | 8/2002 | Reed et al. | |
| 6,432,381 B2 | 8/2002 | Liversidge et al. | |
| 6,458,384 B2 | 10/2002 | Jaenicke et al. | |
| 6,464,958 B1 | 10/2002 | Bernini et al. | |
| 6,482,440 B2 | 11/2002 | Zemlan et al. | |
| 6,524,528 B1 | 2/2003 | Gottuso | |
| 6,528,530 B2 | 3/2003 | Zeitlin et al. | |
| 6,551,612 B2 | 4/2003 | Benowitz | |
| 6,582,285 B2 | 6/2003 | Czekai et al. | |
| 6,592,903 B2 | 7/2003 | Ryde et al. | |
| 6,596,230 B1 | 7/2003 | Woo et al. | |
| 6,607,695 B2 | 8/2003 | Vellutato | |
| 6,635,284 B2 | 10/2003 | Mehta et al. | |
| 6,730,325 B2 | 5/2004 | Devane et al. | |
| 6,793,936 B2 | 9/2004 | Devane et al. | |
| 6,902,742 B2 | 6/2005 | Devane et al. | |
| 2001/0049354 A1 | 12/2001 | Shalaev et al. | |
| 2002/0012675 A1 | 1/2002 | Jain et al. | |
| 2002/0013298 A1 | 1/2002 | Hunter | |
| 2003/0095928 A1 | 5/2003 | McGurk et al. | |
| 2003/0143106 A1 | 7/2003 | Kent et al. | |
| 2003/0185869 A1 | 10/2003 | Wertz et al. | |
| 2003/0219461 A1 | 11/2003 | Britten et al. | |
| 2004/0101560 A1* | 5/2004 | Sawchuk et al. | 424/486 |
| 2004/0106679 A1 | 6/2004 | Klaveness et al. | |
| 2004/0229038 A1 | 11/2004 | Cooper et al. | |
| 2005/0013857 A1* | 1/2005 | Fu et al. | 424/464 |
| 2005/0031691 A1 | 2/2005 | McGurk et al. | |

| | | | |
|---|---|---|---|
| 2005/0063913 A1 | 3/2005 | Pruitt et al. | |
| 2005/0095294 A1 | 5/2005 | Parikh et al. | |
| 2005/0208094 A1* | 9/2005 | Armitage et al. | 424/423 |
| 2005/0267080 A1* | 12/2005 | Kolodney et al. | 514/169 |
| 2006/0009386 A1* | 1/2006 | Stossel et al. | 514/12 |
| 2006/0127468 A1* | 6/2006 | Kolodney et al. | 424/450 |
| 2007/0003615 A1 | 1/2007 | Jenkins et al. | |
| 2007/0003628 A1 | 1/2007 | Liversidge et al. | |

FOREIGN PATENT DOCUMENTS

| | | |
|---|---|---|
| EP | 0274734 A1 | 7/1988 |
| EP | 0202051 B1 | 8/1991 |
| EP | 0502642 A1 | 9/1992 |
| EP | 0338444 B1 | 11/1993 |
| EP | 0601619 A2 | 6/1994 |
| EP | 0605024 A2 | 7/1994 |
| EP | 0636365 A1 | 2/1995 |
| GB | 2179254 A | 3/1987 |
| HU | 202403 B | 4/1998 |
| JP | 61257917 A | 11/1986 |
| JP | 08157392 A | 6/1996 |
| JP | 9500866 A | 1/1997 |
| JP | 2002510318 A | 4/2002 |
| RU | 2069558 C1 | 11/1996 |
| WO | 8909066 A1 | 10/1989 |
| WO | 9204011 A1 | 3/1992 |
| WO | 9428882 A1 | 12/1994 |
| WO | 9703672 A1 | 2/1997 |
| WO | 9703673 A1 | 2/1997 |
| WO | 9725028 A1 | 7/1997 |
| WO | 9732573 A1 | 9/1997 |
| WO | 9806380 A2 | 2/1998 |
| WO | 9814168 A2 | 4/1998 |
| WO | 9817261 A1 | 4/1998 |
| WO | 9828345 A1 | 7/1998 |
| WO | 9833378 A1 | 8/1998 |
| WO | 9901122 A1 | 1/1999 |
| WO | 9902142 A2 | 1/1999 |
| WO | 9903471 A1 | 1/1999 |
| WO | WO9930690 A1 * | 6/1999 |
| WO | 9951209 A1 | 10/1999 |
| WO | 9962496 A1 | 12/1999 |
| WO | 0024383 A1 | 5/2000 |
| WO | 0025746 | 5/2000 |
| WO | 0025752 A1 | 5/2000 |
| WO | 0059479 A1 | 10/2000 |
| WO | 0059481 A1 | 10/2000 |
| WO | 0158433 A1 | 8/2001 |
| WO | 0178689 A2 | 10/2001 |
| WO | 0210120 | 2/2002 |
| WO | 02098565 | 12/2002 |
| WO | WO 2004019901 A2 * | 3/2004 |

OTHER PUBLICATIONS

Rudnic et al., "Oral Solid Dosage Forms," Remington's Pharmaceutical Sciences, Chapter 89, pp. 1633-1658 (Mack Publishing Company, 1990).

Song et al., "Formulation and characterization of biodegradable nanoparticles for intravascular local drug delivery", Journal of Controlled Release, Elsevier Science Publishers B.V., Amsterdam, NL, vol. 43, No. 2-3, Jan. 18, 1997, pp. 197-212, XP004425642, ISSN: 0168-3659.

Reid, "Gamma Processing Technology: An Alternative Technology for Terminal Sterilization of Parenterals", PDA Journal of Pharmaceutical Science and Technology, Bethesda, MD, US, vol. 49, No. 2, 1995, pp. 83-89, XP002087677, ISSN: 1079-7440.

Mohr et al., "Gamma Irradiation for terminal sterilization of 17 beta-estradiol loaded poly-(D,L-lactide-co-glycolide) microparticles", Journal of Controlled Release, Elsevier Science Publishers B.V., Amsterdam, NL, vol. 61, No. 1-2, Aug. 27, 1999, pp. 203-217, XP004362977, ISSN: 0168-3659.

U.S. Appl. No. 60/353,230, Wertz, et al., "Nanoparticulate Compositions Having Lysozyme as a Surface Stabilizer", filed Feb. 4, 2002.

Shah et al., Gel-Matrix Systems Exhibiting Bimodal Controlled Release for Oral Drug Delivery, J. Cont. Rel., 1989, 169-175, 9, Elsevier, Amsterdam, Netherlands.

Giunchedi et al., Ketoprofen Pulsatile Absorption From 'Multiple Unit' Hydrophilic Matrices, Int. J. Pharm., 1991, 177-181, 77, Elsevier.

Conte et al., A New Ibuprofen Pulsed Release Oral Dosage Form, Drug Del. Ind. Pharm., 1989, 2583-2596, 15 (14-16), Marcel Dekker.

Zimm et al., Drug Release From a Multiparticulate Pellet System, Pharma. Dev. Tech., 1996, 37-42, 1(1), Marcel Dekker.

PCT/ISA/210 for PCT/US06/19905 issued Apr. 3, 2008.

F. Hirayama et al., "Cyclodextrin-based controlled drug release system", Adv. Drug Deliv. Rev., Mar. 1, 1999; pp. 125-141, 36(1), Elsevier.

B.V. Manyam et al., "Evaluation of Equivalent Efficacy of Sinemet and Sinemet CR in Patients with Parkinson's Disease Applying Levodopa Dosage Conversion Formula", Clin. Neuropharmacol., Jan.-Feb. 1999, pp. 33-39, 22(1).

G.K. Gourlay, "Sustained Relief of Chronic Pain", Clin. Pharmacokinet., Sep. 1998, pp. 173-190, 35(3), Adis International Ltd.

U. Conte et al., "A New Ibuprofen Pulsed Release Oral Dosage Form", Drug Del. Ind. Pharm., 1989, pp. 2583-2596, 15(14-16), Marcel Dekker Inc.

A. Prakash et al., "Long-Acting Isosorbide Mononitrate", Drugs, Jan. 1999, pp. 93-99, 57(1), Adis International Ltd.

I. R. Wilding, "Evolution of the Biopharmaceutics Classification System (BCS) to oral Modified Release (MR) formulations; what do we need to consider?", Eur. J. Pharm. Sci., Jul. 1999, pp. 157-159, 8(3), Elsevier.

P. Giunchedi et al., "Ketoprofen pulsatile absorption from 'multiple unit' hydrophilic matrices", J. Pharm., 1991, pp. 177-181, 77.

P. Arunothayanun et al., "Extrusion of niosomes from capillaries: approaches to a pulsed delivery device", J. Control Release, Aug. 5, 1999, pp. 391-397, 60(2-3), Elsevier.

G.S. Rekhi et al., "Bioavailability and In-vitro/in-vivo Correlation for Propranolol Hydrochloride Extended-release Bead Products Prepared Using Aqueous Polymeric Dispersions", J. Pharm. Pharmacol., Dec. 1996, pp. 1276-1284, 48(12), The Royal Pharmaceutical Society of Great Britain.

K.S. Murthy et al., "Current Perspectives on the Dissolution Stability of Solid Oral Dosage Forms", J. Pharm. Sci., Feb. 1993, pp. 113-126, 82(2), American Pharmaceutical Association.

K.R. Zimm et al., "Drug Release from a Multiparticulate Pellet System", Pharm. Dev. Technol., Apr. 1996, pp. 37-42, 1 (1), Informa Healthcare, UK.

A.C. Shah et al., "Gel-Matrix Systems Exhibiting Bimodal Controlled Release for Oral Drug Delivery", J. Cont. Rel., 1989, pp. 169-175, 9, Elsevier.

Lippold, B. C., Constant or Pulsed Delivery of Active Substance?, Pharmacie in uns Zeit, Jan. 1990, 13-31, No. 1.

Li, X. et al., Osmotic Controlled Drug Delivery Systems, Design of Controlled Release Drug Delivery Systems, Nov. 2005, 204-229, Chapter 7.

Yuan, J. et al., Formulation Effects on the Thermomechanical Properties and Permeability of Free Films and Coating Films, Pharm. Tech., Mar. 2009, 88-98, vol. 3 No. 3.

Ruddy, S. B. et al., Design and Characterization of a Surfactant-enriched Tablet Formulation for Oral Delivery of a Poorly Water-Soluble Immunosuppressive Agent, Intl. Journal of Pharmaceutics, 1999, 173-186, 182.

* cited by examiner

NANOPARTICULATE AND CONTROLLED RELEASE COMPOSITIONS COMPRISING CEFDITOREN

CROSS REFERENCE TO RELATED APPLICATIONS

The present application is a continuation of U.S. application Ser. No. 11/449,005 filed Jun. 7, 2006, which claims the priority benefit of U.S. provisional Application No. 60/688,613, filed Jun. 7, 2005, and is a continuation-in-part of U.S. application Ser. No. 11/372,857, filed Mar. 10, 2006, which is a continuation-in-part of U.S. application Ser. No. 10/827,689, filed Apr. 19, 2004, which is a continuation of U.S. application Ser. No. 10/354,483, filed Jan. 30, 2003, now U.S. Pat. No. 6,793,936, which is a continuation of U.S. application Ser. No. 10/331,754, filed Dec. 30, 2002, now U.S. Pat. No. 6,902,742, which is a continuation of U.S. application Ser. No. 09/850,425, filed May 7, 2001, now U.S. Pat. No. 6,730,325, which is a continuation of U.S. application Ser. No. 09/566,636, filed May 8, 2000, now U.S. Pat. No. 6,228,398, which is a continuation of International Application No. PCT/US99/25632, filed Nov. 1, 1999, which claims the priority of U.S. provisional Application No. 60/106,726, filed Nov. 2, 1998.

FIELD OF INVENTION

The present invention relates to compositions and methods for the prevention and treatment of infections and related conditions. In particular, the present invention relates to a composition comprising a cefditoren, or a salt, derivative, prodrug, or other form thereof, for example cefditoren pivoxil, and methods for making and using such a composition. In an embodiment of the invention, the composition is in nanoparticulate form and comprises also at least one surface stabilizer. The present invention relates also to novel dosage forms for the controlled delivery of cefditoren, or a salt, derivative, prodrug, or other form thereof, for example cefditoren pivoxil.

BACKGROUND OF THE INVENTION

Cefditoren pivoxil, chemically known as (−)-(6R,7R)-2,2-dimethylpropionyloxymethyl 7-[(Z)-2-(2-aminothiazol-4-yl)-2-methoxyiminoacetamido]-3-[(Z)-2-(4-methylthiazol-5-yl)ethenyl]-8-oxo-5-thia-1-azabicyclo[4.2.0]oct-2-ene-2-carboxylate, is an orally deliverable, third-generation cephalosporin. The empirical formula is $C_{25}H_{28}N_6O_7S_3$ and the molecular weight is 620.73.

The chemical structure of cefditoren pivoxil is shown below:

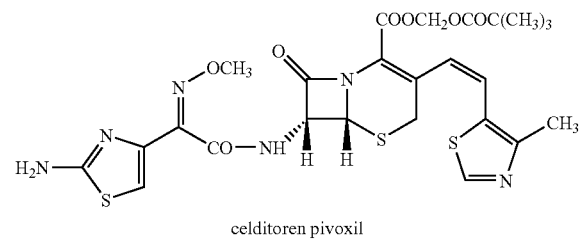

celditoren pivoxil

Cefditoren pivoxil is a semi-synthetic cephalosporin antibiotic for oral administration. It is a prodrug which is hydrolyzed by gastro-intestinal esterases in the stomach and small intestine during absorption to form active cefditoren. Cefditoren is distributed in the circulating blood. The amorphous form of cefditoren pivoxil developed for clinical use is a light yellow powder. It is freely soluble in dilute hydrochloric acid and soluble at levels equal to 6.06 mg/mL in ethanol and <0.1 mg/mL in water.

Cefditoren pivoxil may be administered as part of a dosage form marketed by TAP Pharmaceuticals Inc. under the registered trademark name SPECTRACEF®. SPECTRACEF® tablets contain 200 mg of cefditoren as cefditoren pivoxil and inactive ingredients such as croscarmellose sodium, sodium caseinate (a milk protein), D-mannitol, magnesium stearate, sodium tripolyphosphate, hydroxypropyl methylcellulose, and hydroxypropyl cellulose. The tablet coating contains hydroxypropyl methylcellulose, titanium dioxide, polyethylene glycol, and carnauba wax. Tablets are printed with ink containing FD&C Blue No. 1, D&C Red No. 27, shellac, and propylene glycol.

Cefditoren pivoxil is indicated for the treatment of mild to moderate infections in humans caused by susceptible strains of certain microorganisms in conditions such as acute bacterial exacerbation of chronic bronchitis caused by *Haemophilus influenzae* (including (beta)-lactamase-producing strains), *Haemophilus parainfluenzae* (including (beta)-lactamase-producing strains), *Streptococcus pneumoniae* (penicillin-susceptible strains only), or *Moraxella catarrhalis* (including (beta)-lactamase-producing strains); community-acquired pneumonia caused by *Haemophilus influenzae* (including (beta)-lactamase-producing strains), *Haemophilus parainfluenzae* (including (beta)-lactamase-producing strains), *Streptococcus pneumoniae* (penicillin-susceptible strains only), or *Moraxella catarrhalis* (including (beta)-lactamase-producing strains); pharyngitis/tonsillitis caused by *Streptococcus pyogenes*; and uncomplicated skin and skin-structure infections caused by *Staphylococcus aureus* (including (beta)-lactamase-producing strains) or *Streptococcus pyogenes*.

Cephalosporin compounds and their use have been described, for example, in U.S. Pat. No. 4,839,350 for "Cephalosporin Compounds and the Production Thereof," U.S. Pat. No. 4,918,068 for "Cephem Compounds," and U.S. Pat. No. 5,958,915 for "Antibacterial Composition for Oral Administration" which patents are hereby incorporated by reference.

Cefditoren exhibits poor bioavailability when taken orally and, as such, cefditoren pivoxil is generally prescribed to be taken with food to enhance absorption. Additionally, conventional cefditoren pivoxil tablets must generally be administered three times a day for the treatment of bacterial infections. The present invention addresses such problems by providing nanoparticulate compositions containing cefditoren, or a salt, derivative, prodrug, or other form thereof, for example cefditoren pivoxil, which overcome the poor bioavailability of cefditoren and eliminate the requirement to take the product with food. The present invention also provides a controlled release composition comprising cefditoren, or a salt, derivative, prodrug, or other form thereof, for example cefditoren picoxil, which eliminates the need to take cefditoren more than once a day, thereby increasing patient convenience and compliance.

SUMMARY OF THE INVENTION

The present invention relates to a nanoparticulate composition comprising: (A) cefditoren, or a salt, derivative, prodrug, other form thereof, for example cefditoren pivoxil; and (B) at least one surface stabilizer. The composition may optionally comprise also a pharmaceutically acceptable carrier and any desired excipients. The surface stabilizer can be adsorbed on or associated with the surface of the nanoparticulate particles. The nanoparticulate particles have an effective average particle size of less than about 2,000 nm. A preferred dosage form of the invention is a solid dosage form, although any pharmaceutically acceptable dosage form can be utilized.

A preferred dosage form of the invention is a solid dosage form, although any pharmaceutically-acceptable dosage form may be utilized.

One embodiment of the invention encompasses a nanoparticulate composition comprising cefditoren, or a salt, derivative, prodrug, or other form thereof, for example cefditoren pivoxil, wherein the pharmacokinetic profile of the cefditoren, or a salt, derivative, prodrug, or other form thereof, following administration of the composition to a subject, is not affected by the fed or fasted state of the subject.

In yet another embodiment, the invention encompasses a nanoparticulate composition comprising cefditoren, or a salt, derivative, prodrug, or other form thereof, for example cefditoren pivoxil, wherein administration of the composition to a subject in a fasted state is bioequivalent to administration of the composition to a subject in a fed state.

Another embodiment of the invention is directed to a nanoparticulate composition comprising cefditoren, or a salt, derivative, prodrug, or other form thereof, for example cefditoren pivoxil, and comprising also one or more additional compounds useful in the prevention and treatment of infections and other related conditions.

This invention further provides a method of making the inventive nanoparticulate composition. Such a method comprises contacting nanoparticulate particles comprising cefditoren, or a salt, derivative, prodrug, or other form thereof, for example cefditoren pivoxil, with at least one surface stabilizer for a period of time and under conditions sufficient to provide a stabilized nanoparticulate composition comprising cefditoren, or a salt, derivative, prodrug, or other form thereof, for example cefditoren pivoxil.

The present invention is also directed to methods of treatment including but not limited to, the prevention and treatment of infections and other related disease states using the novel nanoparticulate compositions disclosed herein. Such methods comprise administering to a subject a therapeutically effective amount of such a composition. Other methods of treatment using the nanoparticulate compositions of the invention are known to those of skill in the art.

The present invention further relates to a controlled release composition comprising cefditoren, or a salt, derivative, prodrug, or other form thereof, for example cefditoren pivoxil, which in operation produces a plasma profile substantially similar to the plasma profile produced by the administration of two or more IR dosage form of cefditoren, or a salt, derivative, prodrug, or other form thereof, given sequentially. Cefditoren, or a salt, derivative, prodrug, or other form thereof, may be contained in nanoparticulate particles which comprise also at least one surface stabilizer.

Conventional frequent dosage regimes in which an immediate release (IR) dosage form is administered at periodic intervals typically give rise to a pulsatile plasma profile. In this case, a peak in the concentration of cefditoren, or a salt, derivative, prodrug, or other form thereof, is observed after administration of each IR dose with troughs (regions of low concentration of ceditoren, or the salt, derivative, prodrug, or other form thereof) developing between consecutive administration time points. Such dosage regimes (and their resultant pulsatile plasma profiles) have particular pharmacological and therapeutic effects associated with them. For example, the wash out period provided by the fall off of the plasma concentration of the active between peaks has been thought to be a contributing factor in reducing or preventing patient tolerance to cefditoren, or the salt, derivative, prodrug, or other form thereof.

The present invention further relates to a controlled release composition comprising cefditoren, or a salt, derivative, prodrug, or other form thereof, for example cefditoren pivoxil, which in operation produces a plasma profile that eliminates the "peaks" and "troughs" produced by the administration of two or more IR dosage forms of the drug given sequentially if such a profile is beneficial. This type of profile can be obtained using a controlled release mechanism that allows for continuous delivery. The cefditoren, or a salt, derivative, prodrug, or other form thereof may be contained in nanoparticulate particles which comprise also at least one surface stabilizer.

Multiparticulate modified controlled release compositions similar to those disclosed herein are disclosed and claimed in the U.S. Pat. Nos. 6,228,398 and 6,730,325 to Devane et al; both of which are incorporated by reference herein. All of the relevant prior art in this field may also be found therein.

It is a further object of the invention to provide a controlled release composition which in operation delivers cefditoren, or a salt, derivative, prodrug, or other form thereof, for example cefditoren pivoxil, or nanoparticles containing the same, in a pulsatile manner or a continuous manner.

Another object of the invention is to provide a controlled release composition which substantially mimics the pharmacological and therapeutic effects produced by the administration of two or more IR dosage forms given sequentially.

Another object of the invention is to provide a controlled release composition which substantially reduces or eliminates the development of patient tolerance to cefditoren, or a salt, derivative, prodrug, or other form thereof, for example cefditoren pivoxil.

Another object of the invention is to provide a controlled release composition which releases an active ingredient therein in a bimodal manner. This may be accomplished, for example, in a composition in which a first portion of the active ingredient of the composition is released immediately upon administration and a second portion of the active ingredient is released rapidly after an initial delay period.

Another object of the invention is to formulate the dosage forms of cefditoren, or a salt, derivative, prodrug, or other form thereof, for example cefditoren pivoxil, as an erodable formulation, a diffusion controlled formulation, or an osmotic controlled formulation.

Another object of the invention is to provide a controlled release composition capable of releasing cefditoren, or a salt, derivative, prodrug, or other form thereof, for example cefditoren pivoxil, or nanoparticles containing the same, in a bimodal or multi-modal manner in which a first portion of the cefditoren, or a salt, derivative, prodrug, or other form thereof, or nanoparticles containing the same, is released either immediately or after a delay time to provide a pulse of release and one or more additional portions of the cefditoren, or a salt, derivative, prodrug, or other form thereof, or nanoparticles containing the same, is released, after a respective lag time, to provide additional pulses of release during a period of up to twenty-four hours.

Another object of the invention is to provide solid oral dosage forms comprising a controlled release composition comprising cefditoren, or a salt, derivative, prodrug, or other form thereof, for example cefditoren pivoxil. The cefditoren, or a salt, derivative, prodrug, or other form thereof, may be contained in nanoparticulate particles which comprise also at least one surface stabilizer.

Other objects of the invention include provision of a once daily dosage form of cefditoren, or a salt, derivative, prodrug, or other form thereof, for example cefditoren pivoxil, which, in operation, produces a plasma profile substantially similar to the plasma profile produced by the administration of two immediate release dosage forms thereof given sequentially and a method for prevention and treatment of infections or related conditions based on the administration of such a dosage form. Cefditoren, or a salt, derivative, prodrug, or other form thereof, for example cefditoren pivoxil, may be contained in nanoparticulate particles which comprise also at least one surface stabilizer.

The above objects are realized by a controlled release composition having a first component comprising a first population of cefditoren, or a salt, derivative, prodrug, or other form thereof, for example cefditoren pivoxil, or nanoparticles containing the same, and a second component or formulation comprising a second population of a cefditoren, or a salt, derivative, prodrug, or other form thereof, for example cefditoren pivoxil, or nanoparticulates containing the same. The ingredient-containing particles of the second component further comprises a modified release constituent comprising a release coating or release matrix material, or both. Following oral delivery, the composition in operation delivers the cefditoren, or a salt, derivative, prodrug, or other form thereof, or nanoparticulates containing the same, in a pulsatile or continuous manner.

The present invention utilizes controlled release delivery of cefditoren, or a salt, derivative, prodrug, or other form thereof, for example cefditoren pivoxil, or nanoparticulates containing the same, from a solid oral dosage formulation, to allow dosage less frequently than before, and preferably once-a-day administration, increasing patient convenience and compliance. The mechanism of controlled release would preferably utilize, but not be limited to, erodable formulations, diffusion controlled formulations and osmotic controlled formulations. A portion of the total dose may be released immediately to allow for rapid onset of effect. The invention is useful in improving patient compliance and, therefore, therapeutic outcome for all treatments requiring a cefditoren, or a salt, derivative, prodrug, or other form thereof, including but not limited to, the prevention and treatment of infective conditions. This approach can replace conventional cefditoren tablets and solutions, which are administered multiple times daily as adjunctive therapy in the prevention and treatment of infective symptoms.

The present invention also relates to a controlled modified release composition for the controlled release of cefditoren, or a salt, derivative, prodrug, or other form thereof, for example cefditoren pivoxil, or nanoparticles containing the same. In particular, the present invention relates to a controlled release composition that in operation delivers cefditoren, or a salt, derivative, prodrug, or other form thereof, for example cefditoren pivoxil, or nanoparticles containing the same, in a pulsatile or continuous manner, preferably during a period of up to twenty-four hours.

The present invention further relates to solid oral dosage forms containing a controlled release composition.

Preferred controlled release formulations are erodable formulations, diffusion controlled formulations and osmotic controlled formulations. According to the invention, a portion of the total dose may be released immediately to allow for rapid onset of effect, with the remaining portion of the total dose released over an extended time period. The invention is useful in improving compliance and, therefore, therapeutic outcome for all treatments requiring a cefditoren, or a salt, derivative, prodrug, or other form thereof including but not limited to, prevention and treatment of infective conditions.

The present invention relates also to multiparticulate compositions of the type described above in which the nanoparticulate particles themselves form the particles of the multiparticulate.

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

The present invention is described herein using several definitions, as set forth below and throughout the application.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, the phrase "therapeutically effective amount" shall mean the dosage that provides the specific pharmacological response for which the cefditoren, or a salt, derivative, prodrug, or other form thereof, is administered in a significant number of subjects in need of the relevant treatment. It is emphasized that a therapeutically effective amount of cefditoren, or a salt, derivative, prodrug, or other form thereof, that is administered to a particular subject in a particular instance will not always be effective in treating the conditions described herein, even though such dosage is deemed to be a therapeutically effective amount by those of skill in the art.

The term "prodrug" as used herein when referring to a prodrug of cefditoren refers to a compound which, following administration to a subject, is metabolized to form active cefitoren.

The term "particulate" as used herein refers to a state of matter which is characterized by the presence of discrete particles, pellets, beads or granules irrespective of their size, shape or morphology.

The term "multiparticulate" as used herein means a plurality of discrete, or aggregated, particles, pellets, beads, granules or mixture thereof irrespective of their size, shape or morphology. A composition comprising a multiparticulate is described herein as a "multiparticulate composition".

The term "nanoparticulate" refers to a multiparticulate in which the "effective average particle size" (see below) of the particles therein is less than about 2000 nm (2 microns) in diameter. A composition comprising a nanoparticulate is described herein as a "nanoparticulate composition".

The phrase "effective average particle size" as used herein to describe a multiparticulate (e.g., a nanoparticulate) means that at least 50% of the particles therein are of a specified size. Accordingly, "effective average particle size of less than about 2000 nm in diameter" means that at least 50% of the particles therein are less than about 2000 nm in diameter.

"D50" refers to the particle size below which 50% of the particles in a multiparticulate fall. Similarly, "D90" is the particle size below which 90% of the particles in a multiparticulate fall.

As used herein with reference to stable particles, "stable" connotes, but is not limited to one or more of the following parameters: (1) the particles do not appreciably flocculate or agglomerate due to interparticle attractive forces or otherwise significantly increase in particle size over time; (2) the physical structure of the particles is not altered over time, such as by conversion from an amorphous phase to a crystalline phase; (3) the particles are chemically stable; and/or (4) where the cefditoren, or a salt, derivative, prodrug, or other form thereof, has not been subject to a heating step at or above the melting point of the particles in the preparation of the nanoparticles of the present invention.

The phrase "poorly water soluble drug" refers to a drug that has a solubility in water of less than about 30 mg/ml, less than about 20 mg/ml, less than about 10 mg/ml, or less than about 1 mg/ml.

The term "modified release" as used herein includes a release which is not immediate and includes controlled release, extended release, sustained release and delayed release.

The term "time delay" as used herein refers to the period of time between the administration of a dosage form comprising the composition of the invention and the release of the active ingredient from a particular component thereof.

The term "lag time" as used herein refers to the time between the release of the active ingredient from one component of the composition and the release of the active ingredient from another component of the composition.

The term "erodable" as used herein refers to formulations which may be worn away, diminished, or deteriorated by the action of substances within the body.

The term "diffusion controlled" as used herein refers to formulations which may spread as the result of their spontaneous movement, for example, from a region of higher to one of lower concentration.

The term "osmotic controlled" as used herein refers to formulations which may spread as the result of their movement through a semi-permeable membrane into a solution of higher concentration that tends to equalize the concentrations of the formulation on the two sides of the membrane.

I. Nanoparticulate Compositions Comprising a Cefditoren, or a Salt, Derivative, Prodrug, or Other Form Thereof The present invention provides a nanoparticulate composition comprising particles which comprise: (A) cefditoren, or a salt, derivative, prodrug, or other form thereof, for example cefditoren pivoxil; and (B) at least one surface stabilizer. Nanoparticulate compositions were first described in U.S. Pat. No. 5,145,684. Nanoparticulate active agent compositions are described also in, for example, U.S. Pat. Nos. 5,298,262; 5,302,401; 5,318,767; 5,326,552; 5,328,404; 5,336,507; 5,340,564; 5,346,702; 5,349,957; 5,352,459; 5,399,363; 5,494,683; 5,401,492; 5,429,824; 5,447,710; 5,451,393; 5,466,440; 5,470,583; 5,472,683; 5,500,204; 5,518,738; 5,521,218; 5,525,328; 5,543,133; 5,552,160; 5,565,188; 5,569,448; 5,571,536; 5,573,749; 5,573,750; 5,573,783; 5,580,579; 5,585,108; 5,587,143; 5,591,456; 5,593,657; 5,622,938; 5,628,981; 5,643,552; 5,718,388; 5,718,919; 5,747,001; 5,834,025; 6,045,829; 6,068,858; 6,153,225; 6,165,506; 6,221,400; 6,264,922; 6,267,989; 6,270,806; 6,316,029; 6,375,986; 6,428,814; 6,431,478; 6,432,381; 6,582,285; 6,592,903; 6,656,504; 6,742,734; 6,745,962; 6,811,767; 6,908,626; 6,969,529; 6,976,647; and 6,991,191; and U.S. Patent Publication Nos. 20020012675; 20050276974; 20050238725; 20050233001; 20050147664; 20050063913; 20050042177; 20050031691; 20050019412; 20050004049; 20040258758; 20040258757; 20040229038; 20040208833; 20040195413; 20040156895; 20040156872; 20040141925; 20040115134; 20040105889; 20040105778; 20040101566; 20040057905; 20040033267; 20040033202; 20040018242; 20040015134; 20030232796; 20030215502; 20030185869; 20030181411; 20030137067; 20030108616; 20030095928; 20030087308; 20030023203; 20020179758; 20020012675; and 20010053664. Amorphous small particle compositions are described, for example, in U.S. Pat. Nos. 4,783,484; 4,826,689; 4,997,454; 5,741,522; 5,776,496.

As stated above, the effective average particle size of the particles in the nanoparticulate composition of the present invention is less than about 2000 nm (i.e., 2 microns) in diameter. In embodiments of the present invention, the effective average particle size may be, for example, less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm in diameter, as measured by light-scattering methods, microscopy, or other appropriate methods.

The nanoparticulate particles may exist in a crystalline phase, an amorphous phase, a semi-crystalline phase, a semi amorphous phase, or a mixture thereof.

In addition to allowing for a smaller solid dosage form size, the nanoparticulate composition of the present invention exhibits increased bioavailability, and requires smaller doses of the cefditoren, or a salt, derivative, prodrug, or other form thereof, as compared to prior conventional, non-nanoparticulate compositions which comprise a cefditoren, or a salt, derivative, prodrug, or other form thereof. In one embodiment of the invention, the cefditoren, or a salt, derivative, prodrug, or other form thereof, when administered in the nanoparticulate composition of the present invention, has a bioavailability that is about 50% greater than the cefditoren, or a salt, derivative, prodrug, or other form thereof, when administered in a conventional dosage form. In other embodiments, the cefditoren, or a salt, derivative, prodrug, or other form thereof, when administered in the nanoparticulate composition of the present invention, has a bioavailability that is about 40% greater, about 30% greater, about 20% or about 10% greater than the cefditoren, or a salt, derivative, prodrug, or other form thereof, when administered in a conventional dosage form.

The nanoparticulate composition preferably also has a desirable pharmacokinetic profile as measured following the initial dosage thereof to a mammalian subject. The desirable pharmacokinetic profile of the composition includes, but is not limited to: (1) a $C_{max}$ for cefditoren, or a salt, derivative, prodrug, or other form thereof, when assayed in the plasma of a mammalian subject following administration, that is preferably greater than the $C_{max}$ for the same cefditoren, or a salt, derivative, prodrug, or other form thereof, delivered at the same dosage by a non-nanoparticulate composition; and/or (2) an AUC for cefditoren, or a salt, derivative, prodrug, or other form thereof, when assayed in the plasma of a mammalian subject following administration, that is preferably greater than the AUC for the same cefditoren, or a salt, derivative, prodrug, or other form thereof, delivered at the same dosage by a non-nanoparticulate composition; and/or (3) a $T_{max}$ for cefditoren, or a salt, derivative, prodrug, or other form thereof, when assayed in the plasma of a mammalian subject following administration, that is preferably less than the $T_{max}$ for the same cefditoren, or a salt, derivative, prodrug, or other form thereof, delivered at the same dosage by a non-nanoparticulate composition.

In an embodiment of the present invention, a nanoparticulate composition of the present invention exhibits, for example, a $T_{max}$ for cefditoren, or a salt, derivative, prodrug, or other form thereof, contained therein which is not greater than about 90% of the $T_{max}$ for the same cefditoren, or a salt, derivative, prodrug, or other form thereof, delivered at the same dosage by a non-nanoparticulate composition. In other embodiments of the present invention, the nanoparticulate composition of the present invention may exhibit, for example, a $T_{max}$ for cefditoren, or a salt, derivative, prodrug, or other form thereof, contained therein which is not greater than about 80%, not greater than about 70%, not greater than about 60%, not greater than about 50%, not greater than about 30%, not greater than about 25%, not greater than about 20%, not greater than about 15%, not greater than about 10%, or not greater than about 5% of the $T_{max}$ for the same cefditoren, or a salt, derivative, prodrug, or other form thereof, delivered at the same dosage by a non-nanoparticulate composition. In one embodiment of the invention, the $T_{max}$ of cefditoren, or a salt, derivative, prodrug, or other form thereof, when assayed in the plasma of the mammalian subject, is less than about 6 to about 8 hours after administration. In other embodiments of the invention, the $T_{max}$ of cefditoren, or a salt, derivative, prodrug, or other form thereof, is less than about 6 hours, less than about 5 hours, less than about 4 hours, less than about 3 hours, less than about 2 hours, less than about 1 hour, or less than about 30 minutes after administration.

In an embodiment of the present invention, a nanoparticulate composition of the present invention exhibits, for example, a $C_{max}$ for cefditoren, or a salt, derivative, prodrug, or other form thereof, contained therein which is at least about 50% of the $C_{max}$ for the same cefditoren, or a salt, derivative, prodrug, or other form thereof, delivered at the same dosage by a non-nanoparticulate composition. In other embodiments of the present invention, the nanoparticulate composition of the present invention may exhibit, for example, a $C_{max}$ for cefditoren, or a salt, derivative, prodrug, or other form thereof, contained therein which is at least about 100%, at least about 200%, at least about 300%, at least about 400%, at least about 500%, at least about 600%, at least about 700%, at least about 800%, at least about 900%, at least about 1000%, at least about 1100%, at least about 1200%, at least about 1300%, at least about 1400%, at least about 1500%, at least about 1600%, at least about 1700%, at least about 1800%, or at least about 1900% greater than the $C_{max}$ for the same cefditoren, or a salt, derivative, prodrug, or other form thereof, delivered at the same dosage by a non-nanoparticulate composition.

In an embodiment of the present invention, a nanoparticulate composition of the present invention exhibits, for example, an AUC for cefditoren, or a salt, derivative, prodrug, or other form thereof, contained therein which is at least about 25% greater than the AUC for the same cefditoren, or a salt, derivative, prodrug, or other form thereof, delivered at the same dosage by a non-nanoparticulate composition. In other embodiments of the present invention, the nanoparticulate composition of the present invention may exhibit, for example, an AUC for cefditoren, or a salt, derivative, prodrug, or other form thereof, contained therein which is at least about 50%, at least about 75%, at least about 100%, at least about 125%, at least about 150%, at least about 175%, at least about 200%, at least about 225%, at least about 250%, at least about 275%, at least about 300%, at least about 350%, at least about 400%, at least about 450%, at least about 500%, at least about 550%, at least about 600%, at least about 650%, at least about 700%, at least about 750%, at least about 800%, at least about 850%, at least about 900%, at least about 950%, at least about 1000%, at least about 1050%, at least about 1100%, at least about 1150%, or at least about 1200% greater than the AUC for the same cefditoren, or a salt, derivative, prodrug, or other form thereof, delivered at the same dosage by a non-nanoparticulate composition.

The invention encompasses a nanoparticulate composition wherein the pharmacokinetic profile of cefditoren, or a salt, derivative, prodrug, or other form thereof, following administration is not substantially affected by the fed or fasted state of a subject ingesting the composition. This means that there is no substantial difference in the quantity of cefditoren, or a salt, derivative, prodrug, or other form thereof, absorbed or the rate of absorption when the nanoparticulate composition is administered in the fed versus the fasted state. In conventional cefditoren formulations, i.e., SPECTRAFEC®, the absorption of cefditoran is increased when administered with food. This difference in absorption observed with conventional cefditoran formulations is undesirable. The composition of the invention overcomes this problem.

Benefits of a dosage form which substantially eliminates the effect of food include an increase in subject convenience, thereby increasing subject compliance, as the subject does not need to ensure that they are taking a dose either with or without food. This is significant as, with poor subject compliance, an increase in the medical condition for which the cefditoren, or a salt, derivative, prodrug, or other form thereof, is being prescribed may be observed.

The invention encompasses also a nanoparticulate composition comprising the cefditoren, or a salt, derivative, prodrug, or other form thereof, in which administration of the composition to a subject in a fasted state is bioequivalent to administration of the composition to a subject in a fed state.

The difference in absorption of the composition of the invention, when administered in the fed versus the fasted state, preferably is less than about 60%, less than about 55%, less than about 50%, less than about 45%, less than about 40%, less than about 35%, less than about 30%, less than about 25%, less than about 20%, less than about 15%, less than about 10%, less than about 5%, or less than about 3%.

In one embodiment of the invention, the invention encompasses a composition comprising cefditoren, or a salt, derivative, prodrug, or other form thereof, wherein the administration of the composition to a subject in a fasted state is bioequivalent to administration of the composition to a subject in a fed state, in particular as defined by $C_{max}$ and AUC guidelines given by the U.S. Food and Drug Administration and the corresponding European regulatory agency (EMEA). Under U.S. FDA guidelines, two products or methods are bioequivalent if the 90% Confidence Intervals (CI) for AUC and $C_{max}$ are between 0.80 to 1.25 ($T_{max}$ measurements are not relevant to bioequivalence for regulatory purposes). To show bioequivalency between two compounds or administration conditions pursuant to Europe's EMEA guidelines, the 90% CI for AUC must be between 0.80 to 1.25 and the 90% CI for $C_{max}$ must between 0.70 to 1.43.

The nanoparticulate composition of the invention is proposed to have an unexpectedly dramatic dissolution profile. Rapid dissolution of cefditoren, or a salt, derivative, prodrug, or other form thereof, is preferable, as faster dissolution generally leads to faster onset of action and greater bioavailability. To improve the dissolution profile and bioavailability of the cefditoren, or a salt, derivative, prodrug, or other form thereof, it would be useful to increase the drug's dissolution so that it could attain a level close to 100%.

The compositions of the invention preferably have a dissolution profile in which within about 5 minutes at least about 20% of the composition is dissolved. In other embodiments of the invention, at least about 30% or at least about 40% of the composition is dissolved within about 5 minutes. In yet other embodiments of the invention, preferably at least about 40%, at least about 50%, at least about 60%, at least about 70%, or at least about 80% of the composition is dissolved within about 10 minutes. Finally, in another embodiment of the invention, preferably at least about 70%, at least about 80%, at least about 90%, or at least about 100% of the composition is dissolved within about 20 minutes.

Dissolution is preferably measured in a medium which is discriminating. Such a dissolution medium will produce two very different dissolution curves for two products having very different dissolution profiles in gastric juices; i.e., the dissolution medium is predictive of in vivo dissolution of a composition. An exemplary dissolution medium is an aqueous medium containing the surfactant sodium lauryl sulfate at 0.025 M. Determination of the amount dissolved can be carried out by spectrophotometry. The rotating blade method (European Pharmacopoeia) can be used to measure dissolution.

An additional feature of the nanoparticulate composition of the invention is that particles thereof redisperse so that the particles have an effective average particle size of less than about 2000 nm in diameter. This is significant because, if the particles did not redisperse so that they have an effective average particle size of less than about 2000 nm in diameter, the composition may lose the benefits afforded by formulating the cefditoren, or a salt, derivative, prodrug, or other form thereof, therein into a nanoparticulate form. This is because nanoparticulate compositions benefit from the small size of the particles comprising the cefditoren, or a salt, derivative, prodrug, or other form thereof. If the particles do not redisperse into small particle sizes upon administration, then "clumps" or agglomerated particles are formed, owing to the extremely high surface free energy of the nanoparticulate system and the thermodynamic driving force to achieve an overall reduction in free energy. With the formation of such agglomerated particles, the bioavailability of the dosage form may fall well below that observed with the liquid dispersion form of the nanoparticulate composition.

In other embodiments of the invention, the redispersed particles of the invention (redispersed in water, a biorelevant media, or any other suitable liquid media) have an effective average particle size of less than about less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm in diameter, as measured by light-scattering methods, microscopy, or other appropriate methods. Such methods suitable for measuring effective average particle size are known to a person of ordinary skill in the art.

Redispersibility can be tested using any suitable means known in the art. See e.g., the example sections of U.S. Pat. No. 6,375,986 for "Solid Dose Nanoparticulate Compositions Comprising a Synergistic Combination of a Polymeric Surface Stabilizer and Dioctyl Sodium Sulfosuccinate."

The nanoparticulate composition of the present invention exhibits dramatic redispersion of the particles upon administration to a mammal, such as a human or animal, as demonstrated by reconstitution/redispersion in a biorelevant aqueous media, such that the effective average particle size of the redispersed particles is less than about 2000 nm. Such biorelevant aqueous media can be any aqueous media that exhibits the desired ionic strength and pH, which form the basis for the biorelevance of the media. The desired pH and ionic strength are those that are representative of physiological conditions found in the human body. Such biorelevant aqueous media can be, for example, aqueous electrolyte solutions or aqueous solutions of any salt, acid, or base, or a combination thereof, which exhibit the desired pH and ionic strength.

Biorelevant pH is well known in the art. For example, in the stomach, the pH ranges from slightly less than 2 (but typically greater than 1) up to 4 or 5. In the small intestine the pH can range from 4 to 6, and in the colon it can range from 6 to 8. Biorelevant ionic strength is also well known in the art. Fasted state gastric fluid has an ionic strength of about 0.1M while fasted state intestinal fluid has an ionic strength of about 0.14. See e.g., Lindahl et al., "Characterization of Fluids from the Stomach and Proximal Jejunum in Men and Women," Pharm. Res., 14 (4): 497-502 (1997). It is believed that the pH and ionic strength of the test solution is more critical than the specific chemical content. Accordingly, appropriate pH and ionic strength values can be obtained through numerous combinations of strong acids, strong bases, salts, single or multiple conjugate acid-base pairs (i.e., weak acids and corresponding salts of that acid), monoprotic and polyprotic electrolytes, etc.

Representative electrolyte solutions can be, but are not limited to, HCl solutions, ranging in concentration from about 0.001 to about 0.1 N, and NaCl solutions, ranging in concentration from about 0.001 to about 0.1 M, and mixtures thereof. For example, electrolyte solutions can be, but are not limited to, about 0.1 N HCl or less, about 0.01 N HCl or less, about 0.001 N HCl or less, about 0.1 M NaCl or less, about 0.01 M NaCl or less, about 0.001 M NaCl or less, and mixtures thereof. Of these electrolyte solutions, 0.01 M HCl and/or 0.1 M NaCl, are most representative of fasted human physiological conditions, owing to the pH and ionic strength conditions of the proximal gastrointestinal tract.

Electrolyte concentrations of 0.001 N HCl, 0.01 N HCl, and 0.1 N HCl correspond to pH 3, pH 2, and pH 1, respectively. Thus, a 0.01 N HCl solution simulates typical acidic conditions found in the stomach. A solution of 0.1 M NaCl provides a reasonable approximation of the ionic strength conditions found throughout the body, including the gastrointestinal fluids, although concentrations higher than 0.1 M may be employed to simulate fed conditions within the human GI tract.

Exemplary solutions of salts, acids, bases or combinations thereof, which exhibit the desired pH and ionic strength, include but are not limited to phosphoric acid/phosphate salts+sodium, potassium and calcium salts of chloride, acetic acid/acetate salts+sodium, potassium and calcium salts of chloride, carbonic acid/bicarbonate salts+sodium, potassium and calcium salts of chloride, and citric acid/citrate salts+sodium, potassium and calcium salts of chloride.

As stated above, the composition comprises also at least one surface stabilizer. The surface stabilizer can be adsorbed on or associated with the surface of the cefditoren, or a salt, derivative, prodrug, or other form thereof. Preferably, the surface stabilizer adheres on, or associates with, the surface of the particles, but does not react chemically with the particles or with other surface stabilizer molecules. Individually adsorbed molecules of the surface stabilizer are essentially free of intermolecular cross-linkages.

The relative amounts of the cefditoren, or a salt, derivative, prodrug, or other form thereof, and surface stabilizer present in the composition of the present invention can vary widely.

The optional amount of the individual components can depend, upon, among other things, the particular drug selected, the hydrophilic-lipophilic balance (HLB), melting point, and the surface tension of water solutions of the stabilizer. The concentration of the cefditoren, or a salt, derivative, prodrug, or other form thereof, can vary from about 99.5% to about 0.001%, from about 95% to about 0.1%, or from about 90% to about 0.5%, by weight, based on the total combined weight of the cefditoren, or salt, derivative, prodrug, or other form thereof, and surface stabilizer(s), not including other excipients. The concentration of the surface stabilizer(s) can vary from about 0.5% to about 99.999%, from about 5.0% to about 99.9%, or from about 10% to about 99.5%, by weight, based on the total combined dry weight of the cefditoren, or salt, derivative, prodrug, or other form thereof, and surface stabilizer(s), not including other excipients.

The choice of a surface stabilizer(s) for the cefditoren, or salt, derivative, prodrug, or other form thereof, is non-trivial and required extensive experimentation to realize a desirable formulation. Accordingly, the present invention is directed to the surprising discovery that nanoparticulate compositions comprising cefditoren, or a salt, derivative, prodrug, or other form thereof, can be made.

Combinations of more than one surface stabilizer can be used in the invention. Useful surface stabilizers which can be employed in the invention include, but are not limited to, known organic and inorganic pharmaceutical excipients. Such excipients include various polymers, low molecular weight oligomers, natural products, and surfactants. Surface stabilizers include nonionic, anionic, cationic, ionic, and zwitterionic surfactants.

Representative examples of surface stabilizers include hydroxypropyl methylcellulose (now known as hypromellose), hydroxypropylcellulose, polyvinylpyrrolidone, sodium lauryl sulfate, dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxs 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hypromellose phthalate, noncrystalline cellulose, magnesium aluminium silicate, triethanolamine, polyvinyl alcohol (PVA), 4-(1,1,3, 3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-1OG® or Surfactant 10-G® (Olin Chemicals, Stamford, Conn.); Crodestas SL-40® (Croda, Inc.); and SA9OHCO, which is $C_{18}H_{37}CH_2(CON(CH_3)-CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-phospholipid, PEG-cholesterol, PEG-cholesterol derivative, PEG-vitamin A, PEG-vitamin E, lysozyme, random copolymers of vinyl pyrrolidone and vinyl acetate, and the like.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), and polyvinylpyrrolidone-2-dimethylaminoethyl methacrylate dimethyl sulfate.

Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$-dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl ($C_{12-18}$)dimethylbenzyl ammonium chloride, N-alkyl ($C_{14-18}$) dimethyl-benzyl ammonium chloride, N-tetradecylidmethyl-benzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ and ALKAQUAT™ (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly [diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Nonpolymeric surface stabilizers are any nonpolymeric compound, such benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, and quarternary ammonium compounds of the formula $NR_1R_2R_3^{(+)}$. For compounds of the formula $NR_1R_2R_3R_4^{(+)}$:
  (i) none of $R_1$-$R_4$ are $CH_3$;
  (ii) one of $R_1$-$R_4$ is $CH_3$;
  (iii) three of $R_1$-$R_4$ are $CH_3$;
  (iv) all of $R_1$-$R_4$ are $CH_3$;
  (v) two of $R_1$-$R_4$ are $CH_3$, one of $R_1$-$R_4$ is $C_6H_5CH_2$, and one of $R_1$-$R_4$ is an alkyl chain of seven carbon atoms or less;
  (vi) two of $R_1$-$R_4$ are $CH_3$, one of $R_1$-$R_4$ is $C_6H_5CH_2$, and one of $R_1$-$R_4$ is an alkyl chain of nineteen carbon atoms or more;
  (vii) two of $R_1$-$R_4$ are $CH_3$ and one of $R_1$-$R_4$ is the group $C_6H_5(CH_2)_n$, where n>1;
  (viii) two of $R_1$-$R_4$ are $CH_3$, one of $R_1$-$R_4$ is $C_6H_5CH_2$, and one of $R_1$-$R_4$ comprises at least one heteroatom;
  (ix) two of $R_1$-$R_4$ are $CH_3$, one of $R_1$-$R_4$ is $C_6H_5CH_2$, and one of $R_1$-$R_4$ comprises at least one halogen;
  (x) two of $R_1$-$R_4$ are $CH_3$, one of $R_1$-$R_4$ is $C_6H_5CH_2$, and one of $R_1$-$R_4$ comprises at least one cyclic fragment;
  (xi) two of $R_1$-$R_4$ are $CH_3$ and one of $R_1$-$R_4$ is a phenyl ring; or
  (xii) two of $R_1$-$R_4$ are $CH_3$ and two of $R_1$-$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

The surface stabilizers are commercially available and/or can be prepared by techniques known in the art. Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference.

The compositions of the invention can comprise, in addition to the cefditoren, or salt, derivative, prodrug, or other form thereof, one or more compounds useful in treating infective conditions, or other concurrent condition. The composition may also be administered in conjunction with such a compound. These other active compounds preferably include those useful for treatment of bodily conditions such as headaches, fevers, soreness, and other like conditions that are generally occasioned with the onset of infection. Such active compounds should be present in a manner, as determined by one skilled in the art, such that they do not interfere with the therapeutic effect of cefditoren, or a salt, derivative, prodrug, or other form thereof.

The composition of the present invention may comprise also one or more binding agents, filling agents, diluents, lubricating agents, emulsifying and suspending agents, sweeteners, flavoring agents, preservatives, buffers, wetting agents, disintegrants, effervescent agents, perfuming agents, and other excipients. Such excipients are known in the art. In addition, prevention of the growth of microorganisms can be ensured by the addition of various antibacterial and antifungal agents, such as parabens, chlorobutanol, phenol, sorbic acid, and the like. For use in injectable formulations, the composition may comprise also isotonic agents, such as sugars, sodium chloride, and the like and agents for use in delaying the absorption of the injectable pharmaceutical form, such as aluminum monostearate and gelatin.

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™).

Suitable lubricants, including agents that act on the flowability of the powder to be compressed, are colloidal silicon dioxide, such as Aerosil® 200, talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The composition of the present invention may comprise also a carrier, adjuvant, or a vehicle (hereafter, collectively, "carriers").

The nanoparticulate compositions can be made using, for example, milling, homogenization, precipitation, freezing, or template emulsion techniques. Exemplary methods of making nanoparticulate compositions are described in the '684 patent. Methods of making nanoparticulate compositions are described also in U.S. Pat. Nos. 5,518,187; 5,718,388; 5,862,999; 5,665,331; 5,662,883; 5,560,932; 5,543,133; 5,534,270; 5,510,118; and 5,470,583.

In one method, particles comprising cefditoren, or a salt, derivative, prodrug, or other form thereof, are dispersed in a liquid dispersion medium in which the cefditoren, or salt, derivative, prodrug, or other form thereof, is poorly soluble. Mechanical means are then used in the presence of grinding media to reduce the particle size to the desired effective average particle size. The dispersion medium can be, for example, water, safflower oil, ethanol, t-butanol, glycerin, polyethylene glycol (PEG), hexane, or glycol. A preferred dispersion medium is water. The particles can be reduced in size in the presence of at least one surface stabilizer. The particles comprising the cefditoren, or salt, derivative, prodrug, or other form thereof, can be contacted with one or more surface stabilizers after attrition. Other compounds, such as a diluent, can be added to the composition during the size reduction process. Dispersions can be manufactured continuously or in a batch mode. One skilled in the art would understand that it may be the case that, following milling, not all particles may be reduced to the desired size. In such an event, the particles of the desired size may be separated and used in the practice of the present invention.

Another method of forming the desired nanoparticulate composition is by microprecipitation. This is a method of preparing stable dispersions of poorly soluble cefditoren, or a salt, derivative, prodrug, or other form thereof, in the presence of surface stabilizer(s) and one or more colloid stability-enhancing surface active agents free of any trace toxic solvents or solubilized heavy metal impurities. Such a method comprises, for example: (1) dissolving cefditoren, or a salt, derivative, prodrug, or other form thereof, in a suitable solvent; (2) adding the formulation from step (1) to a solution comprising at least one surface stabilizer; and (3) precipitating the formulation from step (2) using an appropriate nonsolvent. The method can be followed by removal of any formed salt, if present, by dialysis or diafiltration and concentration of the dispersion by conventional means.

A nanoparticulate composition may be formed also by homogenization. Exemplary homogenization methods are described in U.S. Pat. No. 5,510,118, for "Process of Preparing Therapeutic Compositions Containing Nanoparticles." Such a method comprises dispersing particles comprising cefditoren, or a salt, derivative, prodrug, or other form thereof, in a liquid dispersion medium, followed by subjecting the dispersion to homogenization to reduce the particle size to the desired effective average particle size. The particles can be reduced in size in the presence of at least one surface stabilizer. The particles can be contacted with one or more surface stabilizers either before or after attrition. Other compounds, such as a diluent, can be added to the composition before, during, or after the size reduction process. Dispersions can be manufactured continuously or in a batch mode.

Another method of forming the desired nanoparticulate composition is by spray freezing into liquid (SFL). This technology comprises injecting an organic or organoaqueous solution of the cefditoren, or a salt, derivative, prodrug, or other form thereof, and surface stabilizer(s) into a cryogenic liquid, such as liquid nitrogen. The droplets of the drug-containing solution freeze at a rate sufficient to minimize crystallization and particle growth, thus formulating nanostructured particles. Depending on the choice of solvent system and processing conditions, the particles can have varying particle morphology. In the isolation step, the nitrogen and solvent are removed under conditions that avoid agglomeration or ripening of the particles.

As a complementary technology to SFL, ultra rapid freezing (URF) may also be used to create equivalent nanostructured particles with greatly enhanced surface area. URF comprises taking a water-miscible, anhydrous, organic, or organoaqueous solution of cefditoren, or a salt, derivative, prodrug, or other form thereof, and surface stabilizer(s) and applying it onto a cryogenic substrate. The solvent is then removed by means such as lyophilization or atmospheric freeze-drying with the resulting nanostructured particles remaining.

Another method of forming the desired nanoparticulate composition is by template emulsion. Template emulsion creates nano-structured particles with controlled particle size distribution and rapid dissolution performance. The method comprises preparing an oil-in-water emulsion and then swelling it with a non-aqueous solution comprising cefditoren, or a salt, derivative, prodrug, or other form thereof, and surface stabilizer(s). The size distribution of the particles is a direct result of the size of the emulsion droplets prior to loading of the emulsion with the drug. The particle size can be controlled and optimized in this process. Furthermore, through selected use of solvents and stabilizers, emulsion stability is achieved with no or suppressed Ostwald ripening. Subsequently, the solvent and water are removed, and the stabilized nano-structured particles are recovered. Various particle morphologies can be achieved by appropriate control of processing conditions.

The invention provides a method comprising the administration of an effective amount of a nanoparticulate composition comprising cefditoren, or a salt, derivative, prodrug, or other form thereof.

The composition of the present invention can be formulated for administration parentally (e.g., intravenous, intramuscular, or subcutaneous), orally (e.g., in solid, liquid, or aerosol form, vaginal), nasally, rectally, ocularly, locally (e.g., in powder, ointment, or drop form), buccally, intracistemally, intraperitoneally, or topically, and the like.

The nanoparticulate composition can be utilized in solid or liquid dosage formulations, such as liquid dispersions, gels, aerosols, ointments, creams, controlled release formulations, fast melt formulations, lyophilized formulations, tablets, capsules, delayed release formulations, extended release formulations, pulsatile release formulations, mixed immediate release and controlled release formulations, etc.

Compositions suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

Solid dosage forms for oral administration include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof. A solid dose tablet formulation is preferred. In such solid dosage forms, the active agent is admixed with at least one of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the cefditoren, or a salt, derivative, prodrug, or other form thereof, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

One of ordinary skill will appreciate that a therapeutically effective amount of cefditoren, or a salt, derivative, prodrug, or other form thereof, can be determined empirically. Actual dosage levels of the cefditoren, or salt, derivative, prodrug, or other form thereof, in the nanoparticulate compositions of the invention may be varied to obtain an amount of the drug that is effective to obtain a desired therapeutic response for a particular composition and method of administration. The selected dosage level therefore depends upon the desired therapeutic effect, the route of administration, the potency of the administered cefditoren, or a salt, derivative, prodrug, or other form thereof, the desired duration of treatment, and other factors.

Dosage unit compositions may contain such amounts of cefditoren, or salt, derivative, prodrug, or other form thereof, or such submultiples thereof as may be used to make up the daily dose. It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex, and diet of the patient; the time of administration, route of administration, and rate of excretion of the cefditoren, or a salt, derivative, prodrug, or other form thereof; the duration of the treatment; active compound used in combination or coincidental with cefditoren, or a salt, derivative, prodrug, or other form thereof; and like factors well known in the medical arts.

II. Controlled Release Compositions Comprising Cefditoren, or a Salt, Derivative, Prodrug, or Other Form Thereof As used in the present application, the term "active agent" may refer to: cefditoren, or a salt, derivative, prodrug, or other form thereof; nanoparticles comprising cefditoren, or a salt, derivative, prodrug, or other form thereof; or any other compound that has a pharmaceutical affect.

The effectiveness of pharmaceutical compounds in the prevention and treatment of disease states depends on a variety of factors including the rate and duration of delivery of the compound from the dosage form to the patient. The combination of delivery rate and duration exhibited by a given dosage form in a patient can be described as its in vivo release profile and, depending on the pharmaceutical compound administered, will be associated with a concentration and duration of the pharmaceutical compound in the blood plasma, referred to as a plasma profile. As pharmaceutical compounds vary in their pharmacokinetic properties such as bioavailability, and rates of absorption and elimination, the release profile and the resultant plasma profile become important elements to consider in designing effective therapies.

The release profiles of dosage forms may exhibit different rates and durations of release and may be continuous or pulsatile. Continuous release profiles include release profiles in which a quantity of one or more pharmaceutical compounds is released continuously throughout the dosing interval at either a constant or variable rate. Pulsatile release profiles include release profiles in which at least two discrete quantities of one or more pharmaceutical compounds are released at different rates and/or over different time frames. For any given pharmaceutical compound or combination of such compounds, the release profile for a given dosage form gives rise to an associated plasma profile in a patient. When two or more components of a dosage form have different release profiles, the release profile of the dosage form as a whole is a combination of the individual release profiles and may be described generally as "multimodal." The release profile of a two-component dosage form in which each component has a different release profile may described as "bimodal," and the release profile of a three-component dosage form in which each component has a different release profile may described as "trimodal."

Similar to the variables applicable to the release profile, the associated plasma profile in a patient may exhibit constant or variable blood plasma concentration levels of the pharmaceutical compounds over the duration of action and may be continuous or pulsatile. Continuous plasma profiles include plasma profiles of all rates and duration which exhibit a single plasma concentration maximum. Pulsatile plasma profiles include plasma profiles in which at least two higher blood plasma concentration levels of pharmaceutical compound are separated by a lower blood plasma concentration level and may be described generally as "multimodal." Pulsatile plasma profiles exhibiting two peaks may be described as "bimodal" and plasma profiles exhibiting three peaks may be described as "trimodal." Depending on, at least in part, the pharmacokinetics of the pharmaceutical compounds included in the dosage form as well as the release profiles of the individual components of the dosage form, a multimodal release profile may result in either a continuous or a pulsatile plasma profile upon administration to a patient.

In one embodiment, the present invention provides a multiparticulate modified release composition which delivers cefditoren, or a salt, derivative, prodrug, or other form thereof, for example cefditoren pivoxil, or nanoparticles containing the cefditoren, or a salt, derivative, prodrug, or other form thereof, in a pulsatile manner. The nanoparticles are of the type described above and comprise also at least one surface stabilizer.

In still another embodiment, the present invention provides a multiparticulate modified release composition which delivers the cefditoren, or a salt, derivative, prodrug, or other form thereof, for example cefditoren pivoxil, or nanoparticles containing the cefditoren, or a salt, derivative, prodrug, or other form thereof, in a continuous manner. The nanoparticles are of the type described above and comprise also at least one surface stabilizer.

In yet another embodiment, the present invention provides a multiparticulate modified release composition in which a first portion of the cefditoren, or a salt, derivative, prodrug, or other form thereof, for example cefditoren pivoxil, or nanoparticles containing the cefditoren, or a salt, derivative, prodrug, or other form thereof, is released immediately upon administration and one or more subsequent portions of the cefditoren, or a salt, derivative, prodrug, or other form thereof, for example cefditoren pivoxil, or nanoparticles containing the cefditoren, or a salt, derivative, prodrug, or other form thereof, are released after an initial time delay.

In yet another embodiment, the present invention provides solid oral dosage forms for once-daily or twice-daily administration comprising the multiparticulate modified release composition of the present invention.

In still another embodiment, the present invention provides a method for the prevention and/or treatment of infections and other related diseases comprising the administration of a composition of the present invention.

In an embodiment, the present invention provides a multiparticulate modified release composition in which the particles forming the multiparticulate are nanoparticulate particles of the type described above. The nanoparticulate particles may, as desired, contain a modified release coating and/or a modified release matrix material.

In an embodiment, the cefditoren, or a salt, derivative, prodrug, or other form thereof used in the compositions described herein is cefditoren pivoxil.

According to one aspect of the present invention, there is provided a pharmaceutical composition having a first component comprising active ingredient-containing particles, and at least one subsequent component comprising active ingredient-containing particles, each subsequent component having a rate and/or duration of release different from the first component wherein at least one of said components comprises particles containing cefditoren, or a salt, derivative, prodrug, or other form thereof, for example cefditoren pivoxil. In an embodiment of the invention, the cefditoren, or a salt, derivative, prodrug, or other form thereof-containing particles that form the multiparticulate may themselves contain nanoparticulate particles of the type described above which comprise the cefditoren, or a salt, derivative, prodrug, or other form thereof and also at least one surface stabilizer. In another embodiment of the invention, nanoparticulate particles of the type described above which comprise the cefditoren, or a salt, derivative, prodrug, or other form thereof and also at least one surface stabilizer themselves are the drug-containing particles of the multiparticulate. The drug-containing particles may be coated with a modified release coating. Alternatively or additionally, the drug-containing particles may comprise a modified release matrix material. Following oral delivery, the composition delivers the cefditoren, or a salt, derivative, prodrug, or other form thereof, or nanoparticles containing the cefditoren, or a salt, derivative, prodrug, or other form thereof, in a pulsatile manner. In one embodiment, the first component provides an immediate release of the cefditoren, or a salt, derivative, prodrug, or other form thereof, or nanoparticles containing the cefditoren, or a salt, derivative, prodrug, or other form thereof, and the one or more subsequent components provide a modified release of the cefditoren, or a salt, derivative, prodrug, or other form thereof, or nanoparticles containing the cefditoren, or a salt, derivative, prodrug, or other form thereof. In such embodiments, the immediate release component serves to hasten the onset of action by minimizing the time from administration to a therapeutically effective plasma concentration level, and the one or more subsequent components serve to minimize the variation in plasma concentration levels and/or maintain a therapeutically effective plasma concentration throughout the dosing interval.

The modified release coating and/or the modified release matrix material cause a lag time between the release of the active ingredient from the first population of active ingredient-containing particles and the release of the active ingredient from subsequent populations of active ingredient-containing particles. Where more than one population of active ingredient-containing particles provide a modified release, the modified release coating and/or the modified release matrix material causes a lag time between the release of the active ingredient from the different populations of active ingredient-containing particles. The duration of these lag times may be varied by altering the composition and/or the amount of the modified release coating and/or altering the composition and/or amount of modified release matrix material utilized. Thus, the duration of the lag time can be designed to mimic a desired plasma profile.

Because the plasma profile produced by the modified release composition upon administration is substantially similar to the plasma profile produced by the administration of two or more IR dosage forms given sequentially, the modified release composition of the present invention is particularly useful for administering a cefditoren, or a salt, derivative, prodrug, or other form thereof.

According to another aspect of the present invention, the composition can be designed to produce a plasma profile that minimizes or eliminates the variations in plasma concentration levels associated with the administration of two or more IR dosage forms given sequentially. In such embodiments, the composition may be provided with an immediate release component to hasten the onset of action by minimizing the time from administration to a therapeutically effective plasma concentration level, and at least one modified release component to maintain a therapeutically effective plasma concentration level throughout the dosing interval.

The active ingredients in each component may be the same or different. For example, the composition may comprise components comprising only the cefditoren, or a salt, derivative, prodrug, or other form thereof, or nanoparticles containing the cefditoren, or a salt, derivative, prodrug, or other form thereof, as the active ingredient. Alternatively, the composition may comprise a first component comprising the cefditoren, or a salt, derivative, prodrug, or other form thereof, or nanoparticles containing the cefditoren, or a salt, derivative, prodrug, or other form thereof, and at least one subsequent component comprising an active ingredient other than the cefditoren, or a salt, derivative, prodrug, or other form thereof, or nanoparticles containing the cefditoren, or a salt, derivative, prodrug, or other form thereof, suitable for co-administration with the cefditoren, or a salt, derivative, prodrug, or other form thereof, or a first component containing an active ingredient other than the cefditoren, or a salt, derivative, prodrug, or other form thereof, or nanoparticles containing the cefditoren, or a salt, derivative, prodrug, or other form thereof, and at least one subsequent component comprising the cefditoren, or a salt, derivative, prodrug, or other form thereof, or nanoparticles containing the cefditoren, or a salt, derivative, prodrug, or other form thereof. Indeed, two or more active ingredients may be incorporated into the same component when the active ingredients are compatible with each other. An active ingredient present in one component of the composition may be accompanied by, for example, an enhancer compound or a sensitizer compound in another component of the composition, in order to modify the bioavailability or therapeutic effect thereof.

As used herein, the term "enhancer" refers to a compound which is capable of enhancing the absorption and/or bioavailability of an active ingredient by promoting net transport across the GIT in an animal, such as a human. Enhancers include but are not limited to medium chain fatty acids; salts, esters, ethers and derivatives thereof, including glycerides and triglycerides; non-ionic surfactants such as those that can be prepared by reacting ethylene oxide with a fatty acid, a fatty alcohol, an alkylphenol or a sorbitan or glycerol fatty acid ester; cytochrome P450 inhibitors, P-glycoprotein inhibitors and the like; and mixtures of two or more of these agents.

In those embodiments in which more than one drug-containing component is present, the proportion of cefditoren, or a salt, derivative, prodrug, or other form thereof contained in each component may be the same or different depending on the desired dosing regime. The cefditoren, or a salt, derivative, prodrug, or other form thereof present in the first component and in subsequent components may be any amount sufficient to produce a therapeutically effective plasma concentration level. The cefditoren, or a salt, derivative, prodrug, or other form thereof, when applicable, may be present either in the form of one substantially optically pure stereoisomer or as a mixture, racemic or otherwise, of two or more stereoisomers. The cefditoren, or a salt, derivative, prodrug, or other form thereof is preferably present in the composition in an amount of from about 0.1 to about 500 mg, preferably in the amount of from about 1 to about 100 mg. The cefditoren, or a salt, derivative, prodrug, or other form thereof is preferably present in the first component in an amount of from about 0.5 to about 60 mg; more preferably the cefditoren, or a salt, derivative, prodrug, or other form thereof, is present in the first component in an amount of from about 2.5 to about 30 mg. The cefditoren, or a salt, derivative, prodrug, or other form thereof is present in subsequent components in an amount within similar ranges to those described for the first component.

The time release characteristics for the delivery of the cefditoren, or a salt, derivative, prodrug, or other form thereof from each of the components may be varied by modifying the composition of each component, including modifying any of the excipients and/or coatings which may be present. In particular, the release of the cefditoren, or a salt, derivative, prodrug, or other form thereof, or nanoparticles containing the cefditoren, or a salt, derivative, prodrug, or other form thereof, may be controlled by changing the composition and/or the amount of the modified release coating on the particles, if such a coating is present. If more than one modified release component is present, the modified release coating for each of these components may be the same or different. Similarly, when modified release is facilitated by the inclusion of a modified release matrix material, release of the active ingredient may be controlled by the choice and amount of modified release matrix material utilized. The modified release coating may be present, in each component, in any amount that is sufficient to yield the desired delay time for each particular component. The modified release coating may be preset, in each component, in any amount that is sufficient to yield the desired time lag between components.

The lag time and/or time delay for the release of the cefditoren, or a salt, derivative, prodrug, or other form thereof from each component may also be varied by modifying the composition of each of the components, including modifying any excipients and coatings which may be present. For example, the first component may be an immediate release component wherein the cefditoren, or a salt, derivative, prodrug, or other form thereof, or nanoparticles containing the cefditoren, or a salt, derivative, prodrug, or other form thereof, is released immediately upon administration. Alternatively, the first component may be, for example, a time-delayed immediate release component in which the cefditoren, or a salt, derivative, prodrug, or other form thereof, or nanoparticles containing the cefditoren, or a salt, derivative, prodrug, or other form thereof, is released substantially in its entirety immediately after a time delay. The second and subsequent component may be, for example, a time-delayed immediate release component as just described or, alternatively, a time-delayed sustained release or extended release component in which the cefditoren, or a salt, derivative, prodrug, or other form thereof, or nanoparticles containing the cefditoren, or a salt, derivative, prodrug, or other form thereof, is released in a controlled fashion over an extended period of time.

As will be appreciated by those skilled in the art, the exact nature of the plasma concentration curve will be influenced by the combination of all of these factors just described. In particular, the lag time between the delivery (and thus also the onset of action) of the cefditoren, or a salt, derivative, prodrug, or other form thereof, or nanoparticles containing the cefditoren, or a salt, derivative, prodrug, or other form thereof, in each component may be controlled by varying the composition and coating (if present) of each of the components. Thus by variation of the composition of each component (including the amount and nature of the active ingredient(s)) and by variation of the lag time, numerous release and plasma profiles may be obtained. Depending on the duration of the lag time between the release of the cefditoren, or a salt, derivative, prodrug, or other form thereof, or nanoparticles containing the cefditoren, or a salt, derivative, prodrug, or other form thereof, from each component and the nature of the release of the cefditoren, or a salt, derivative, prodrug, or other form thereof, or nanoparticles containing the cefditoren, or a salt, derivative, prodrug, or other form thereof, from each component (i.e. immediate release, sustained release etc.), the plasma profile may be continuous (i.e., having a single maximum) or pulsatile in which the peaks in the plasma profile may be well separated and clearly defined (e.g. when the lag time is long) or superimposed to a degree (e.g. when the lag time is short).

The plasma profile produced from the administration of a single dosage unit comprising the composition of the present invention is advantageous when it is desirable to deliver two or more pulses of active ingredient without the need for administration of two or more dosage units.

Any coating material which modifies the release of the cefditoren, or a salt, derivative, prodrug, or other form thereof in the desired manner may be used. In particular, coating materials suitable for use in the practice of the present invention include but are not limited to polymer coating materials, such as cellulose acetate phthalate, cellulose acetate trimaletate, hydroxy propyl methylcellulose phthalate, polyvinyl acetate phthalate, ammonio methacrylate copolymers such as those sold under the trademark Eudragit® RS and RL, poly acrylic acid and poly acrylate and methacrylate copolymers such as those sold under the trademark Eudragit® S and L, polyvinyl acetaldiethylamino acetate, hydroxypropyl methylcellulose acetate succinate, shellac; hydrogels and gel-forming materials, such as carboxyvinyl polymers, sodium alginate, sodium carmellose, calcium carmellose, sodium carboxymethyl starch, polyvinyl alcohol, hydroxyethyl cellulose, methyl cellulose, gelatin, starch, and cellulose based cross-linked polymers—in which the degree of crosslinking is low so as to facilitate adsorption of water and expansion of the polymer matrix, hydroxypropyl cellulose, hydroxypropyl methylcellulose, polyvinylpyrrolidone, crosslinked starch, microcrystalline cellulose, chitin, aminoacryl-methacrylate copolymer (Eudragit® RS-PM, Rohm & Haas), pullulan, collagen, casein, agar, gum arabic, sodium carboxymethyl cellulose, (swellable hydrophilic polymers) poly(hydroxyalkyl methacrylate) (mol. wt. ~5 k-5,000 k), polyvinylpyrrolidone (mol. wt. ~10 k-360 k), anionic and cationic hydrogels, polyvinyl alcohol having a low acetate residual, a swellable mixture of agar and carboxymethyl cellulose, copolymers of maleic anhydride and styrene, ethylene, propylene or isobutylene, pectin (mol. wt. ~30 k-300 k), polysaccharides such as agar, acacia, karaya, tragacanth, algins and guar, polyacrylamides, Polyox® polyethylene oxides (mol. wt. ~100 k-5,000 k), AquaKeep® acrylate polymers, diesters of polyglucan, crosslinked polyvinyl alcohol and poly N-vinyl-2-pyrrolidone, sodium starch glucolate (e.g. Explotab®; Edward Mandell C. Ltd.); hydrophilic polymers such as polysaccharides, methyl cellulose, sodium or calcium carboxymethyl cellulose, hydroxypropyl methyl cellulose, hydroxypropyl cellulose, hydroxyethyl cellulose, nitro cellulose, carboxymethyl cellulose, cellulose ethers, polyethylene oxides (e.g. Polyox®, Union Carbide), methyl ethyl cellulose, ethylhydroxy ethylcellulose, cellulose acetate, cellulose butyrate, cellulose propionate, gelatin, collagen, starch, maltodextrin, pullulan, polyvinyl pyrrolidone, polyvinyl alcohol, polyvinyl acetate, glycerol fatty acid esters, polyacrylamide, polyacrylic acid, copolymers of methacrylic acid or methacrylic acid (e.g. Eudragit®, Rohm and Haas), other acrylic acid derivatives, sorbitan esters, natural gums, lecithins, pectin, alginates, ammonia alginate, sodium, calcium, potassium alginates, propylene glycol alginate, agar, and gums such as arabic, karaya, locust bean, tragacanth, carrageens, guar, xanthan, scleroglucan and mixtures and blends thereof. As will be appreciated by the person skilled in the art, excipients such as plasticisers, lubricants, solvents and the like may be added to the coating. Suitable plasticisers include for example acetylated monoglycerides; butyl phthalyl butyl glycolate; dibutyl tartrate; diethyl phthalate; dimethyl phthalate; ethyl phthalyl ethyl glycolate; glycerin; propylene glycol; triacetin; citrate; tripropioin; diacetin; dibutyl phthalate; acetyl monoglyceride; polyethylene glycols; castor oil; triethyl citrate; polyhydric alcohols, glycerol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate.

When the modified release component comprises a modified release matrix material, any suitable modified release matrix material or suitable combination of modified release matrix materials may be used. Such materials are known to those skilled in the art. The term "modified release matrix material" as used herein includes hydrophilic polymers, hydrophobic polymers and mixtures thereof which are capable of modifying the release of a cefditoren, or a salt, derivative, prodrug, or other form thereof dispersed therein in vitro or in vivo. Modified release matrix materials suitable for the practice of the present invention include but are not limited to microcrystalline cellulose, sodium carboxymethylcellulose, hydroxyalkylcelluloses such as hydroxypropylmethylcellulose and hydroxypropylcellulose, polyethylene oxide, alkylcelluloses such as methylcellulose and ethylcellulose, polyethylene glycol, polyvinylpyrrolidone, cellulose acteate, cellulose acetate butyrate, cellulose acteate phthalate, cellulose acteate trimellitate, polyvinylacetate phthalate, polyalkylmethacrylates, polyvinyl acetate and mixture thereof.

A modified release composition according to the present invention may be incorporated into any suitable dosage form which facilitates release of the active ingredient in a pulsatile manner. In one embodiment, the dosage form comprises a blend of different populations of active ingredient-containing particles which make up the immediate release and the modified release components, the blend being filled into suitable capsules, such as hard or soft gelatin capsules. Alternatively, the different individual populations of active ingredient-containing particles may be compressed (optionally with additional excipients) into mini-tablets which may be subsequently filled into capsules in the appropriate proportions. Another suitable dosage form is that of a multilayer tablet. In this instance the first component of the modified release composition may be compressed into one layer, with the second component being subsequently added as a second layer of the multilayer tablet. The populations of the particles making up the composition of the invention may further be included in rapidly dissolving dosage forms such as an effervescent dosage form or a fast-melt dosage form.

In one embodiment, the composition comprises at least two components containing cefditoren, or a salt, derivative, prodrug, or other form thereof: a first component and one or more subsequent components. In such embodiment, the first component of the composition may exhibit a variety of release profiles including profiles in which substantially all of the cefditoren, or a salt, derivative, prodrug, or other form thereof, or nanoparticles containing the cefditoren, or a salt, derivative, prodrug, or other form thereof, contained in the first component is released rapidly upon administration of the dosage form, released rapidly but after a time delay (delayed release), or released slowly over time. In one such embodiment, the cefditoren, or a salt, derivative, prodrug, or other form thereof, or nanoparticles containing the cefditoren, or a salt, derivative, prodrug, or other form thereof, contained in the first component is released rapidly upon administration to a patient. As used herein, "released rapidly" includes release profiles in which at least about 80% of the active ingredient of a component is released within about an hour after administration, the term "delayed release" includes release profiles in which the active ingredient of a component is released (rapidly or slowly) after a time delay, and the terms "controlled release" and "extended release" include release profiles in which at least about 80% of the active ingredient contained in a component is released slowly.

The second component of such embodiment may also exhibit a variety of release profiles including an immediate release profile, a delayed release profile or a controlled release profile. In one such embodiment, the second component exhibits a delayed release profile in which the cefditoren, or a salt, derivative, prodrug, or other form thereof, or nanoparticles containing the cefditoren, or a salt, derivative, prodrug, or other form thereof, is released after a time delay.

The plasma profile produced by the administration of dosage forms of the present invention which comprise an immediate release component comprising the cefditoren, or a salt, derivative, prodrug, or other form thereof, or nanoparticles containing the cefditoren, or a salt, derivative, prodrug, or other form thereof, and at least one modified release component comprising the cefditoren, or a salt, derivative, prodrug, or other form thereof, or nanoparticles containing the cefditoren, or a salt, derivative, prodrug, or other form thereof, can be substantially similar to the plasma profile produced by the administration of two or more IR dosage forms given sequentially, or to the plasma profile produced by the administration of separate IR and modified release dosage forms. Accordingly, the dosage forms of the present invention can be particularly useful for administering cefditoren, or a salt, derivative, prodrug, or other form thereof where the maintenance of pharmacokinetic parameters may be desired but is problematic.

In one embodiment, the composition and the solid oral dosage forms containing the composition release the cefditoren, or a salt, derivative, prodrug, or other form thereof, or nanoparticles containing the cefditoren, or a salt, derivative, prodrug, or other form thereof, such that substantially all of the cefditoren, or a salt, derivative, prodrug, or other form thereof, or nanoparticles containing the cefditoren, or a salt, derivative, prodrug, or other form thereof, contained in the first component is released prior to release of the cefditoren, or a salt, derivative, prodrug, or other form thereof, or nanoparticles containing the cefditoren, or a salt, derivative, prodrug, or other form thereof, from the at least one subsequent component. When the first component comprises an IR component, for example, it is preferable that release of the cefditoren, or a salt, derivative, prodrug, or other form thereof, or nanoparticles containing the cefditoren, or a salt, derivative, prodrug, or other form thereof, from the at least one subsequent component is delayed until substantially all the cefditoren, or a salt, derivative, prodrug, or other form thereof, or nanoparticles containing the cefditoren, or a salt, derivative, prodrug, or other form thereof, in the IR component has been released. Release of the cefditoren, or a salt, derivative, prodrug, or other form thereof, or nanoparticles containing the cefditoren, or a salt, derivative, prodrug, or other form thereof, from the at least one subsequent component may be delayed as detailed above by the use of a modified release coatings and/or a modified release matrix material.

When it is desirable to minimize patient tolerance by providing a dosage regime which facilitates wash-out of a first dose of the cefditoren, or a salt, derivative, prodrug, or other form thereof from a patient's system, release of the cefditoren, or a salt, derivative, prodrug, or other form thereof, or nanoparticles containing the cefditoren, or a salt, derivative, prodrug, or other form thereof, from subsequent components may be delayed until substantially all of the cefditoren, or a salt, derivative, prodrug, or other form thereof, or nanoparticles containing the cefditoren, or a salt, derivative, prodrug, or other form thereof, contained in the first component has been released, and further delayed until at least a portion the cefditoren, or a salt, derivative, prodrug, or other form thereof released from the first component has been cleared from the patient's system. In one embodiment, release of the cefditoren, or a salt, derivative, prodrug, or other form thereof, or nanoparticles containing the cefditoren, or a salt, derivative, prodrug, or other form thereof, from subsequent components of the composition is substantially, if not completely, delayed for a period of at least about two hours after administration of the composition. In another embodiment, the release of cefditoren, or a salt, derivative, prodrug, or other form thereof, or nanoparticles containing the cefditoren, or a salt, derivative, prodrug, or other form thereof, from subsequent components of the composition is substantially, if not completely, delayed for a period of at least about four hours after administration of the composition.

As described hereinbelow, the present invention also includes various types of modified release systems by which the cefditoren, or a salt, derivative, prodrug, or other form thereof, or nanoparticles containing the cefditoren, or a salt, derivative, prodrug, or other form thereof, may be delivered in either a pulsatile or continuous manner. These systems include but are not limited to: films with the cefditoren, or a salt, derivative, prodrug, or other form thereof, or nanoparticles containing the cefditoren, or a salt, derivative, prodrug, or other form thereof, in a polymer matrix (monolithic devices); systems in which the cefditoren, or a salt, derivative, prodrug, or other form thereof, or nanoparticles containing the cefditoren, or a salt, derivative, prodrug, or other form thereof, is contained by a polymer (reservoir devices); polymeric colloidal particles or microencapsulates (microparticles, microspheres or nanoparticles) in the form of reservoir and matrix devices; systems in which the cefditoren, or a salt, derivative, prodrug, or other form thereof, or nanoparticles containing the cefditoren, or a salt, derivative, prodrug, or other form thereof, is contained by a polymer which contains a hydrophilic and/or leachable additive e.g., a second polymer, surfactant or plasticizer, etc. to give a porous device, or a device in which cefditoren, or a salt, derivative, prodrug, or other form thereof release may be osmotically controlled (both reservoir and matrix devices); enteric coatings (ionizable and dissolve at a suitable pH); (soluble) polymers with (covalently) attached pendant cefditoren molecules, or a salt, derivative, prodrug, or other form thereof; and devices where release rate is controlled dynamically: e.g., the osmotic pump.

The delivery mechanism of the present invention can control the rate of release of cefditoren, or a salt, derivative, prodrug, or other form thereof, or nanoparticles containing the cefditoren, or a salt, derivative, prodrug, or other form thereof. While some mechanisms will release cefditoren, or a salt, derivative, prodrug, or other form thereof, or nanoparticles containing the cefditoren, or a salt, derivative, prodrug, or other form thereof, at a constant rate, others will vary as a function of time depending on factors such as changing concentration gradients or additive leaching leading to porosity, etc.

Polymers used in sustained release coatings are necessarily biocompatible, and ideally biodegradable. Examples of both naturally occurring polymers such as Aquacoat® (FMC Corporation, Food & Pharmaceutical Products Division, Philadelphia, USA) (ethylcellulose mechanically spheronised to sub-micron sized, aqueous based, pseudo-latex dispersions), and also synthetic polymers such as the Eudragit® (Röhm Pharma, Weiterstadt.) range of poly(acrylate, methacrylate) copolymers are known in the art.

Reservoir Devices

A typical approach to modified release is to encapsulate or contain the drug entirely (e.g., as a core), within a polymer film or coat (i.e., microcapsules or spray/pan coated cores).

The various factors that can affect the diffusion process may readily be applied to reservoir devices (e.g., the effects of additives, polymer functionality (and, hence, sink-solution pH) porosity, film casting conditions, etc.) and, hence, the choice of polymer must be an important consideration in the development of reservoir devices. Modeling the release characteristics of reservoir devices (and monolithic devices) in which the transport of the cefditoren, or a salt, derivative, prodrug, or other form thereof is by a solution-diffusion mechanism therefore typically involves a solution to Fick's second law (unsteady-state conditions; concentration dependent flux) for the relevant boundary conditions. When the device contains dissolved active agent, the rate of release decreases exponentially with time as the concentration (activity) of the agent (i.e., the driving force for release) within the device decreases (i.e., first order release). If, however, the active agent is in a saturated suspension, then the driving force for release is kept constant until the device is no longer saturated. Alternatively the release-rate kinetics may be desorption controlled, and a function of the square root of time.

Transport properties of coated tablets, may be enhanced compared to free-polymer films, due to the enclosed nature of the tablet core (permeant) which may enable the internal build-up of an osmotic pressure which will then act to force the permeant out of the tablet.

The effect of de-ionized water on salt containing tablets coated in poly(ethylene glycol) (PEG)-containing silicone elastomer, and also the effects of water on free films has been investigated. The release of salt from the tablets was found to be a mixture of diffusion through water filled pores, formed by hydration of the coating, and osmotic pumping. KCl transport through films containing just 10% PEG was negligible, despite extensive swelling observed in similar free films, indicating that porosity was necessary for the release of the KCl which then occurred by trans-pore diffusion. Coated salt tablets, shaped as disks, were found to swell in de-ionized water and change shape to an oblate spheroid as a result of the build-up of internal hydrostatic pressure: the change in shape providing a means to measure the force generated. As might be expected, the osmotic force decreased with increasing levels of PEG content. The lower PEG levels allowed water to be imbibed through the hydrated polymer, while the porosity resulting from the coating dissolving at higher levels of PEG content (20 to 40%) allow the pressure to be relieved by the flow of KCl.

Methods and equations have been developed, which by monitoring (independently) the release of two different salts (e.g., KCl and NaCl) allowed the calculation of the relative magnitudes that both osmotic pumping and trans-pore diffusion contributed to the release of salt from the tablet. At low PEG levels, osmotic flow was increased to a greater extent than was trans-pore diffusion due to the generation of only a low pore number density: at a loading of 20%, both mechanisms contributed approximately equally to the release. The build-up of hydrostatic pressure, however, decreased the osmotic inflow, and osmotic pumping. At higher loadings of PEG, the hydrated film was more porous and less resistant to outflow of salt. Hence, although the osmotic pumping increased (compared to the lower loading), trans-pore diffusion was the dominant release mechanism. An osmotic release mechanism has also been reported for microcapsules containing a water soluble core.

Monolithic Devices (Matrix Devices)

Monolithic (matrix) devices may be used for controlling the release of a drug. This is possibly because they are relatively easy to fabricate compared to reservoir devices, and the danger of an accidental high dosage that could result from the rupture of the membrane of a reservoir device is not present. In such a device, the active agent is present as a dispersion within the polymer matrix, and they are typically formed by the compression of a polymer/drug mixture or by dissolution or melting. The dosage release properties of monolithic devices may be dependent upon the solubility of the drug in the polymer matrix or, in the case of porous matrixes, the solubility in the sink solution within the particle's pore network, and also the tortuosity of the network (to a greater extent than the permeability of the film), dependent on whether the drug is dispersed in the polymer or dissolved in the polymer. For low loadings of drug (0 to 5% W/V), the drug will be released by a solution-diffusion mechanism (in the absence of pores). At higher loadings (5 to 10% W/V), the release mechanism will be complicated by the presence of cavities formed near the surface of the device as the drug is lost: such cavities fill with fluid from the environment increasing the rate of release of the drug.

It is common to add a plasticizer (e.g., a poly(ethylene glycol)), a surfactant, or adjuvant (i.e., an ingredient which increases effectiveness), to matrix devices (and reservoir devices) as a means to enhance the permeability (although, in contrast, plasticizers may be fugitive, and simply serve to aid film formation and, hence, decrease permeability—a property normally more desirable in polymer paint coatings). It was noted that the leaching of PEG increased the permeability of (ethyl cellulose) films linearly as a function of PEG loading by increasing the porosity, however, the films retained their barrier properties, not permitting the transport of electrolyte. It was deduced that the enhancement of their permeability was as a result of the effective decrease in thickness caused by the PEG leaching. This was evidenced from plots of the cumulative permeant flux per unit area as a function of time and film reciprocal thickness at a PEG loading of 50% W/W: plots showing a linear relationship between the rate of permeation and reciprocal film thickness, as expected for a (Fickian) solution-diffusion type transport mechanism in a homogeneous membrane. Extrapolation of the linear regions of the graphs to the time axis gave positive intercepts on the time axis: the magnitude of which decreased towards zero with decreasing film thickness. These changing lag times were attributed to the occurrence of two diffusional flows during the early stages of the experiment (the flow of the drug and also the flow of the PEG), and also to the more usual lag time during which the concentration of permeant in the film is building-up. Caffeine, when used as a permeant, showed negative lag times. No explanation of this was forthcoming, but it was noted that caffeine exhibited a low partition coefficient in the system, and that this was also a feature of aniline permeation through polyethylene films which showed a similar negative time lag.

The effects of added surfactants on (hydrophobic) matrix devices has been investigated. It was thought that surfactant may increase the release rate of a drug by three possible mechanisms: (i) increased solubilization, (ii) improved 'wettability' to the dissolution media, and (iii) pore formation as a result of surfactant leaching. For the system studied (Eudragit® RL 100 and RS 100 plasticised by sorbitol, flurbiprofen as the drug, and a range of surfactants) it was concluded that improved wetting of the tablet led to only a partial improvement in drug release (implying that the release was diffusion, rather than dissolution, controlled), although the effect was greater for Eudragit® RS than Eudragit® RL, while the greatest influence on release was by those surfactants that were more soluble due to the formation of disruptions in the matrix allowing the dissolution medium access to within the matrix. This is of obvious relevance to a study of latex films which might be suitable for pharmaceutical coatings, due to the ease with which a polymer latex may be prepared with surfactant as opposed to surfactant-free. Differences were found between the two polymers with only the Eudragit® RS showing interactions between the anionic/cationic surfactant and drug. This was ascribed to the differing levels of quaternary ammonium ions on the polymer.

Composite devices consisting of a polymer/drug matrix coated in a polymer containing no drug also exist. Such a device was constructed from aqueous Eudragit® lattices, and was found to provide a continuous release by diffusion of the drug from the core through the shell. Similarly, a polymer core containing the drug has been produced and coated with a shell that was eroded by gastric fluid. The rate of release of the drug was found to be relatively linear (a function of the rate limiting diffusion process through the shell) and inversely proportional to the shell thickness, whereas the release from the core alone was found to decrease with time.

Microspheres

Methods for the preparation of hollow microspheres have been described. Hollow microspheres were formed by preparing a solution of ethanol/dichloromethane containing the drug and polymer. On pouring into water, an emulsion is formed containing the dispersed polymer/drug/solvent particles, by a coacervation-type process from which the ethanol rapidly diffused precipitating polymer at the surface of the droplet to give a hard-shelled particle enclosing the drug dissolved in the dichloromethane. A gas phase of dichloromethane was then generated within the particle which, after diffusing through the shell, was observed to bubble to the surface of the aqueous phase. The hollow sphere, at reduced pressure, then filled with water which could be removed by a period of drying. No drug was found in the water. Highly porous matrix-type microspheres have also been described. The matrix-type microspheres were prepared by dissolving the drug and polymer in ethanol. On addition to water, the ethanol diffused from the emulsion droplets to leave a highly porous particle. A suggested use of the microspheres was as floating drug delivery devices for use in the stomach.

Pendent Devices

A means of attaching a range of drugs such as analgesics and antidepressants, etc., by means of an ester linkage to poly(acrylate) ester latex particles prepared by aqueous emulsion polymerization has been developed. These lattices, when passed through an ion exchange resin such that the polymer end groups were converted to their strong acid form, could self-catalyze the release of the drug by hydrolysis of the ester link.

Drugs have been attached to polymers, and also monomers have been synthesized with a pendentdrug attached. Dosage forms have been prepared in which the drug is bound to a biocompatible polymer by a labile chemical bond e.g., polyanhydrides prepared from a substituted anhydride (itself prepared by reacting an acid chloride with the drug: methacryloyl chloride and the sodium salt of methoxy benzoic acid) were used to form a matrix with a second polymer (Eudragit® RL) which released the drug on hydrolysis in gastric fluid. The use of polymeric Schiff bases suitable for use as carriers of pharmaceutical amines has also been described.

Enteric Films

Enteric coatings consist of pH sensitive polymers. Typically the polymers are carboxylated and interact very little with water at low pH, while at high pH the polymers ionize causing swelling or dissolving of the polymer. Coatings can therefore be designed to remain intact in the acidic environment of the stomach, protecting either the drug from this environment or the stomach from the drug, but to dissolve in the more alkaline environment of the intestine.

Osmotically Controlled Devices

The osmotic pump is similar to a reservoir device but contains an osmotic agent (e.g., the active agent in salt form) which acts to imbibe water from the surrounding medium via a semi-permeable membrane. Such a device, called an elementary osmotic pump, has been described. Pressure is generated within the device which forces the active agent out of the device via an orifice of a size designed to minimize solute diffusion, while preventing the build-up of a hydrostatic pressure head which can have the effect of decreasing the osmotic pressure and changing the dimensions of the device. While the internal volume of the device remains constant, and there is an excess of solid or saturated solution in the device, then the release rate remains constant delivering a volume equal to the volume of solvent uptake.

Electrically Stimulated Release Devices

Monolithic devices have been prepared using polyelectrolyte gels which swell when, for example, an external electrical stimulus is applied causing a change in pH. The release may be modulated by changes in the applied current to produce a constant or pulsatile release profile.

Hydrogels

In addition to their use in drug matrices, hydrogels find use in a number of biomedical applications such as, for example, soft contact lenses, and various soft implants, and the like.

Methods of Using Modified Release Compositions Comprising Cefditoren, or a Salt, Derivative, Prodrug, or Other Form Thereof According to another aspect of the present invention, there is provided a method for treating a patient suffering from an infection or a related condition comprising the step of administering a therapeutically effective amount of the composition of the present invention in solid oral dosage form. Advantages of the method of the present invention include a reduction in the dosing frequency required by conventional multiple IR dosage regimes while still maintaining the benefits derived from a pulsatile plasma profile or eliminating or minimizing the variations in plasma concentration levels. This reduced dosing frequency is advantageous in terms of patient compliance and the reduction in dosage frequency made possible by the method of the present invention would contribute to controlling health care costs by reducing the amount of time spent by health care workers on the administration of cefditoren, or a salt, derivative, prodrug, or other form thereofs.

In the following examples, all percentages are weight by weight unless otherwise stated. The term "purified water" as used throughout the Examples refers to water that has been purified by passing it through a water filtration system. It is to be understood that the examples are for illustrative purposes only, and should not be interpreted as restricting the spirit and breadth of the invention as defined by the scope of the claims that follow.

EXAMPLES

Examples 1 to 4 provide exemplary cefditoren tablet formulations. These examples are not intended to limit the claims in any respect, but rather to provide exemplary tablet formulations of cefditoren which can be utilized in the methods of the invention. Such exemplary tablets can also comprise a coating agent.

Example 1

Exemplary Nanoparticulate Cefditoren Tablet Formulation #1

| Component | g/Kg |
|---|---|
| Cefditoren | about 50 to about 500 |
| Hypromellose, USP | about 10 to about 70 |
| Docusate Sodium, USP | about 1 to about 10 |
| Sucrose, NF | about 100 to about 500 |
| Sodium Lauryl Sulfate, NF | about 1 to about 40 |
| Lactose Monohydrate, NF | about 50 to about 400 |
| Silicified Microcrystalline Cellulose | about 50 to about 300 |
| Crospovidone, NF | about 20 to about 300 |
| Magnesium Stearate, NF | about 0.5 to about 5 |

Example 2

Exemplary Nanoparticulate Cefditoren Tablet Formulation #2

| Component | Component |
|---|---|
| Cefditoren | about 100 to about 300 |
| Hypromellose, USP | about 30 to about 50 |
| Docusate Sodium, USP | about 0.5 to about 10 |
| Sucrose, NF | about 100 to about 300 |
| Sodium Lauryl Sulfate, NF | about 1 to about 30 |
| Lactose Monohydrate, NF | about 100 to about 300 |
| Silicified Microcrystalline Cellulose | about 50 to about 200 |
| Crospovidone, NF | about 50 to about 200 |
| Magnesium Stearate, NF | about 0.5 to about 5 |

Example 3

Exemplary Nanoparticulate Cefditoren Tablet Formulation #3

| Component | g/Kg |
|---|---|
| Cefditoren | about 200 to about 225 |
| Hypromellose, USP | about 42 to about 46 |
| Docusate Sodium, USP | about 2 to about 6 |
| Sucrose, NF | about 200 to about 225 |
| Sodium Lauryl Sulfate, NF | about 12 to about 18 |
| Lactose Monohydrate, NF | about 200 to about 205 |
| Silicified Microcrystalline Cellulose | about 130 to about 135 |
| Crospovidone, NF | about 112 to about 118 |
| Magnesium Stearate, NF | about 0.5 to about 3 |

Example 4

Exemplary Nanoparticulate Cefditoren Tablet Formulation #4

| Component | g/Kg |
|---|---|
| Cefditoren | about 119 to about 224 |
| Hypromellose, USP | about 42 to about 46 |
| Docusate Sodium, USP | about 2 to about 6 |
| Sucrose, NF | about 119 to about 224 |
| Sodium Lauryl Sulfate, NF | about 12 to about 18 |
| Lactose Monohydrate, NF | about 119 to about 224 |
| Silicified Microcrystalline Cellulose | about 129 to about 134 |
| Crospovidone, NF | about 112 to about 118 |
| Magnesium Stearate, NF | about 0.5 to about 3 |

Example 5

Multiparticulate Modified Release Composition Containing Cefditoren

A multiparticulate modified release composition according to the present invention comprising an immediate release component and a modified release component containing cefditoren is prepared as follows.

(a) Immediate Release Component.

A solution of cefditoren is prepared according to any of the formulations given in Table 1. The methylphenidate solution is then coated onto nonpareil seeds to a level of approximately 16.9% solids weight gain using, for example, a Glatt GPCG3 (Glatt, Protech Ltd., Leicester, UK) fluid bed coating apparatus to form the IR particles of the immediate release component.

TABLE 5

Immediate release component solutions

| | Amount, % (w/w) | |
|---|---|---|
| Ingredient | (i) | (ii) |
| Cefditoren | 13.0 | 13.0 |
| Polyethylene Glycol 6000 | 0.5 | 0.5 |
| Polyvinylpyrrolidone | 3.5 | |
| Purified Water | 83.5 | 86.5 |

(b) Modified Release Component

Cefditoren-containing delayed release particles are prepared by coating immediate release particles prepared according to Example 1(a) above with a modified release coating solution as detailed in Table 2. The immediate release particles are coated to varying levels up to approximately to 30% weight gain using, for example, a fluid bed apparatus.

TABLE 6

Modified release component coating solutions

| | Amount, % (w/w) | | | | | | | |
|---|---|---|---|---|---|---|---|---|
| Ingredient | (i) | (ii) | (iii) | (iv) | (v) | (vi) | (vii) | (viii) |
| Eudragit ® RS 12.5 | 49.7 | 42.0 | 47.1 | 53.2 | 40.6 | — | — | 25.0 |
| Eudragit ® S 12.5 | — | — | — | — | — | 54.35 | 46.5 | — |
| Eudragit ® L 12.5 | — | — | — | — | — | — | 25.0 | |
| Polyvinyl-pyrrolidone | — | — | — | 0.35 | 0.3 | — | — | |
| Diethyl-phthalate | 0.5 | 0.5 | 0.6 | 1.35 | 0.6 | 1.3 | 1.1 | — |

TABLE 6-continued

Modified release component coating solutions

| Ingredient | Amount, % (w/w) | | | | | | | |
|---|---|---|---|---|---|---|---|---|
| | (i) | (ii) | (iii) | (iv) | (v) | (vi) | (vii) | (viii) |
| Triethyl-citrate | — | — | — | — | — | — | — | 1.25 |
| Isopropyl alcohol | 39.8 | 33.1 | 37.2 | 45.1 | 33.8 | 44.35 | 49.6 | 46.5 |
| Acetone | 10.0 | 8.3 | 9.3 | — | 8.4 | — | — | — |
| Talc.sup.1 | — | 16.0 | 5.9 | — | 16.3 | — | 2.8 | 2.25 |

.sup.1 Talc is simultaneously applied during coating for formulations in column (i), (iv) and (vi).

(c) Encapsulation of Immediate and Delayed Release Particles.

The immediate and delayed release particles prepared according to Example 1(a) and (b) above are encapsulated in size 2 hard gelatin capsules to an overall 20 mg dosage strength using, for example, a Bosch GKF 4000S encapsulation apparatus. The overall dosage strength of 20 mg cefditoren was made up of 10 mg from the immediate release component and 10 mg from the modified release component.

Example 6

Multiparticulate Modified Release Composition Containing Cefditoren

Multiparticulate modified release cefditoren compositions according to the present invention having an immediate release component and a modified release component having a modified release matrix material are prepared according to the formulations shown in Table 3(a) and (b).

TABLE 7 (a)

100 mg of IR component is encapsulated with 100 mg of modified release (MR) component to give a 20 mg dosage strength product

| | % (w/w) |
|---|---|
| IR component | |
| Cefditoren | 10 |
| Microcrytalline cellulose | 40 |
| Lactose | 45 |
| Povidone | 5 |
| MR component | |
| Cefditoren | 10 |
| Microcrytalline cellulose | 40 |
| Eudragit ® RS | 45 |
| Povidone | 5 |

TABLE 7 (b)

50 mg of IR component is encapsulated with 50 mg of modified release (MR) component to give a 20 mg dosage strength product.

| | % (w/w) |
|---|---|
| IR component | |
| Cefditoren | 20 |
| Microcrystalline cellulose | 50 |
| Lactose | 28 |
| Povidone | 2 |

TABLE 7 (b)-continued 50 mg of IR component is encapsulated with 50 mg of modified release (MR) component to give a 20 mg dosage strength product.

| | % (w/w) |
|---|---|
| MR component | |
| Cefditoren | 20 |
| Microcrytalline cellulose | 50 |
| Eudragit ® S | 28 |
| Povidone | 2 |

Example 7

The purpose of this prophetic example is to describe how a nanoparticulate ceftidoren composition could be prepared.

An aqueous dispersion of 5% (w/w) ceftidoren, combined with one or more surface stabilizers, such as hydroxypropyl cellulose (HPC-SL) and dioctylsulfosuccinate (DOSS), could be milled in a 10 ml chamber of a NanoMill® 0.01 (NanoMill Systems, King of Prussia, Pa.; see e.g., U.S. Pat. No. 6,431,478), along with 500 micron PolyMill® attrition media (Dow Chemical Co.) (e.g., at an 89% media load). In an exemplary process, the mixture could be milled at a speed of 2500 rpms for 60 minutes.

Following milling, the particle size of the milled ceftidoren particles can be measured, in deionized distilled water, using a Horiba LA 910 particle size analyzer. For a successful composition, the initial mean and/or D50 milled ceftidoren particle size is expected to be less than 2000 nm.

It will be apparent to those skilled in the art that various modifications and variations can be made in the methods and compositions of the present inventions without departing from the spirit or scope of the invention. Thus, it is intended that the present invention cover the modification and variations of the invention provided they come within the scope of the appended claims and their equivalents.

What is claimed is:

1. A stable nanoparticulate composition comprising: (A) particles comprising cefditoren or salts or prodrugs thereof, said particles having an effective average particle size of less than about 2000 nm in diameter; (B) at least one surface stabilizers, adsorbed on the surface of said cefditoren particles, and (C) docusate sodium in sufficient amounts to produce a pharmacokinetic profile wherein the administration of the composition to a subject in a fasted state is bioequivalent to the administration of the composition to a subject in the fed state.

2. The composition of claim 1, wherein said particles are in a crystalline phase, an amorphous phase, a semi-crystalline phase, a semi amorphous phase, or a mixture thereof.

3. The composition of claim 1, wherein the effective average particle size of said particles is selected from the group consisting of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 100 nm, less than about 75 nm, and less than about 50 nm in diameter.

4. The composition of claim 1, wherein the composition is formulated: (A) for administration selected from the group consisting of via injection, oral, vaginal, nasal, rectal, otically, ocular, local, buccal, intracisternal, intraperitoneal, or topically; (B) into a dosage form selected from the group consisting of tablets, capsules, sachets, solutions, dispersions, gels, aerosols, ointments, creams, and mixtures thereof; (C) into a dosage form selected from the group consisting of controlled release formulations, fast melt formulations, lyophilized formulations, delayed release formulations, extended release formulations, pulsatile release formulations, and mixed immediate release and controlled release formulations; or (D) any combination of (A), (B), or (C).

5. The composition of claim 1 further comprising one or more pharmaceutically acceptable excipients, carriers, or a combination thereof.

6. The composition of claim 1, wherein: (A) said cefditoren, or a salt, prodrug thereof is present in said composition in an amount selected from the group consisting of from about 99.5% to about 0.001%, from about 95% to about 0.1%, or from about 90% to about 0.5%, by weight of the total combined dry weight of cefditoren, or a salt, prodrug thereof and surface stabilizer in the composition, not including other excipients; (B) said surface stabilizer or surface stabilizers are present in a total amount of from about 0.5% to about 99.999%, from about 5.0% to about 99.9%, or from about 10% to about 99.5% by weight, based on the total combined dry weight of cefditoren, or a salt, prodrug thereof and surface stabilizer in the composition not including other excipients; or (C) a combination of (A) and (B).

7. The composition of claim 1, wherein the surface stabilizer is selected from the group consisting of a non-ionic surface stabilizer, an anionic surface stabilizer, a cationic surface stabilizer, a zwitterionic surface stabilizer, and an ionic surface stabilizer.

8. The composition of claim 1, wherein the surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hypromellose, carboxymethylcellulose sodium, methylcellulose, hydroxyethylcellulose, hypromellose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers; poloxamines, a charged phospholipid, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl-β-D-thioglucopyranoside; lysozyme, PEG-phospholipid, PEG-cholesterol, PEG-cholesterol derivative, PEG-vitamin A, PEG-vitamin E, lysozyme, random copolymers of vinyl acetate and vinyl pyrrolidone, a cationic polymer, a cationic biopolymer, a cationic polysaccharide, a cationic cellulosic, a cationic alginate, a cationic nonpolymeric compound, a cationic phospholipid, cationic lipids, polymethylmethacrylate trimethylammonium bromide, sulfonium compounds, polyvinylpyrrolidone-2-dimethylaminoethyl methacrylate dimethyl sulfate, hexadecyltrimethyl ammonium bromide, phosphonium compounds, quarternary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$-dimethyl hydroxyethyl ammonium chloride, $C_{12-15}$-dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$) dimethylbenzyl ammonium chloride, N-alkyl ($C_{14-18}$)dimethylbenzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, POLYQUAT 10™, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, MIRAPOL™, ALKAQUAT™, alkyl pyridinium salts; amines, amine salts, amine oxides, imideazolinium salts, protonated quaternary acrylamides, methylated quaternary polymers, and cationic guar.

9. A composition according to claim 1 wherein, upon administration of said composition to a mammal, the composition produces therapeutic results at a dosage which is less than that of a non-nanoparticulate dosage form of the same cefditoren, a salt, or a prodrug thereof.

10. A composition according to claim 1 which has: (a) a Cmax for the cefditoren, or a salt, prodrug thereof, when assayed in the plasma of a mammalian subject following administration, that is greater than the Cmax for the same cefditoren, or a salt, prodrug thereof administered at the same dose using a non-nanoparticulate formulation; (b) an AUC for the cefditoren, or a salt, prodrug thereof, when assayed in the plasma of a mammalian subject following administration, that is greater than the AUC for the same cefditoren, or a salt, prodrug thereof administered at the same dose using a non-nanoparticulate formulation; (c) a Tmax for the cefditoren, or a salt, prodrug thereof, when assayed in the plasma of a mammalian subject following administration, that is less than the Tmax for the same cefditoren, or a salt, prodrug thereof administered at the same dose using a non-nanoparticulate formulation; or (d) any combination of (a), (b), and (c).

11. The composition of claim 1, additionally comprising one or more active compounds useful for the treatment of infections.

12. The composition of claim 11, wherein the one or more active compounds is selected from the group consisting of compounds useful in the treatment of a condition selected from the group consisting of headaches, soreness, fever, and combinations thereof.

13. The composition of claim 1 wherein said cefditoren, is cefditoren pivoxil.

14. A composition according to claim 1 wherein said particles contain a reservoir which contains cefditoren, or a salt, prodrug thereof, said reservoir being enclosed by a semipermeable membrane which allows for water to be imbibed into said particles, thus generating pressure which forces said cefditoren, or a salt, prodrug thereof, out of said particles.

15. A composition according to claim 1 wherein said reservoir comprises also an osmotic agent.

16. A method of preparing the composition of claim 1 comprising contacting particles comprising said cefditoren, or salts or prodrugs or other forms thereof, with at least one surface stabilizer to provide a nanoparticulate composition comprising cefditoren or salts or prodrugs or other forms thereof, having an effective average particle size of less than about 2000 nm in diameter.

17. The method of claim 16, wherein the contacting comprises grinding, wet grinding, homogenization, precipitation, template emulsion, or supercritical fluid particle generation techniques.

18. The method of claim 16, wherein the effective average particle size of the nanoparticulate particles is selected from the group consisting of less than about 1900 nm, less than about 1800 nm, less than about 1700 nm, less than about 1600 nm, less than about 1500 nm, less than about 1000 nm, less than about 1400 nm, less than about 1300 nm, less than about 1200 nm, less than about 1100 nm, less than about 900 nm, less than about 800 nm, less than about 700 nm, less than about 600 nm, less than about 500 nm, less than about 400 nm, less than about 300 nm, less than about 250 nm, less than about 200 nm, less than about 100 nm, less than about 75 nm, and less than about 50 nm in diameter.

19. The method of claim 16 wherein said cefditoren, or salts or prodrugs or other forms thereof is cefditoren pivoxil.

20. A method of treating infections and conditions related thereto comprising administering a composition according to claim 1.

21. The method of claim 20, wherein the effective average particle size of the particles is selected from the group consisting of less than about 1900 nm, less than about 1800 nm, less than about 1700 nm, less than about 1600 nm, less than about 1500 nm, less than about 1000 nm, less than about 1400 nm, less than about 1300 nm, less than about 1200 nm, less than about 1100 nm, less than about 900 nm, less than about 800 nm, less than about 700 nm, less than about 600 nm, less than about 500 nm, less than about 400 nm, less than about 300 nm, less than about 250 nm, less than about 200 nm, less than about 100 nm, less than about 75 nm, and less than about 50 nm in diameter.

22. The method of claim 20 wherein said cefditoren, is cefditoren pivoxil.

* * * * *